United States Patent
Magers et al.

(10) Patent No.: US 10,293,102 B2
(45) Date of Patent: May 21, 2019

(54) PUMP CASSETTES WITH PISTON AND INFUSION PUMP SYSTEMS

(71) Applicant: CareFusion 2200, Inc., San Diego, CA (US)

(72) Inventors: Corey Michael Magers, Oceanside, CA (US); Daniel Toro, Chula Vista, CA (US); Daniel Abal, San Diego, CA (US); Santiago Roman Dodge, Santee, CA (US); Robert Steven Vasko, San Diego, CA (US); Edward Browka, Oneida, NY (US)

(73) Assignee: CareFusion 2200, Inc., San Diego, CA (US)

( * ) Notice: Subject to any disclaimer, the term of this patent is extended or adjusted under 35 U.S.C. 154(b) by 554 days.

(21) Appl. No.: 14/728,911

(22) Filed: Jun. 2, 2015

(65) Prior Publication Data
US 2016/0151564 A1    Jun. 2, 2016

Related U.S. Application Data

(63) Continuation-in-part of application No. 14/557,446, filed on Dec. 1, 2014.

(51) Int. Cl.
A61M 5/145    (2006.01)
A61M 5/36    (2006.01)

(52) U.S. Cl.
CPC ...... *A61M 5/1452* (2013.01); *A61M 5/14586* (2013.01); *A61M 5/365* (2013.01); *A61M 2205/12* (2013.01)

(58) Field of Classification Search
CPC .............. A61M 5/145; A61M 5/16813; A61M 2005/14208; A61M 2005/14288;
(Continued)

(56) References Cited

U.S. PATENT DOCUMENTS

| 4,842,584 A | 6/1989 | Pastrone |
| 5,098,262 A | 3/1992 | Wecker et al. |

(Continued)

FOREIGN PATENT DOCUMENTS

| WO | WO-2005097235 A2 | 10/2005 |
| WO | WO-2014190188 A2 | 11/2014 |
| WO | WO-2016190904 A1 | 12/2016 |

OTHER PUBLICATIONS

International Search Report and Written Opinion for Application No. PCT/US2015/063001, dated Mar. 8, 2016, 22 pages.
(Continued)

*Primary Examiner* — Imani N Hayman
*Assistant Examiner* — Tiffany Legette
(74) *Attorney, Agent, or Firm* — Morgan, Lewis & Bockius LLP

(57) ABSTRACT

Pump cassettes, infusion systems, and methods are described. An example pump cassette may include a rigid body comprising a frame portion, a base portion, a compliant membrane disposed substantially therebetween, and two opposing longitudinal edge sections. The rigid body may include a controllable fluid pathway defined in part by the compliant membrane and extending from an inlet port to an outlet port. The pump cassette may include a piston disposed at least partially within the rigid body such that movement of the piston varies a volume of a pump chamber defined within the controllable fluid pathway.

18 Claims, 15 Drawing Sheets

(58) Field of Classification Search
CPC .......... A61M 2039/226; A61M 5/1413; A61M 5/142; A61M 1/16; A61M 1/28
See application file for complete search history.

(56) References Cited

U.S. PATENT DOCUMENTS

| | | | |
|---|---|---|---|
| 5,554,013 | A | 9/1996 | Owens et al. |
| 5,575,632 | A | 11/1996 | Morris et al. |
| 5,807,075 | A | 9/1998 | Jacobsen et al. |
| 5,816,779 | A | 10/1998 | Lawless et al. |
| 5,954,485 | A | 9/1999 | Johnson et al. |
| 6,475,178 | B1 | 11/2002 | Krajewski et al. |
| 6,494,694 | B2 | 12/2002 | Lawless et al. |
| 7,867,189 | B2 | 1/2011 | Childers et al. |
| 7,972,306 | B2 | 7/2011 | Shearn |
| 8,066,671 | B2 | 11/2011 | Busby et al. |
| 8,465,454 | B2 | 6/2013 | Kirkpatrick |
| 8,523,816 | B2 | 9/2013 | Kirkpatrick |
| 8,668,671 | B2 | 3/2014 | Kirkpatrick |
| 8,771,228 | B2 | 7/2014 | Butterfield |
| 8,784,359 | B2 | 7/2014 | Plahey et al. |
| 8,936,447 | B2 | 1/2015 | Abal |
| 2001/0051789 | A1 | 12/2001 | Parsons |
| 2004/0019313 | A1* | 1/2004 | Childers .............. A61M 1/1696 604/5.01 |
| 2007/0213653 | A1 | 9/2007 | Childers et al. |
| 2008/0138223 | A1 | 6/2008 | Lanigan et al. |
| 2008/0262409 | A1 | 10/2008 | Derrico et al. |
| 2009/0062738 | A1* | 3/2009 | Ziegler ................. A61M 39/24 604/151 |
| 2010/0286599 | A1 | 11/2010 | Ziegler et al. |
| 2011/0040244 | A1 | 2/2011 | Busby et al. |
| 2011/0092894 | A1 | 4/2011 | McGill et al. |
| 2011/0178359 | A1 | 7/2011 | Hirschman et al. |
| 2011/0282276 | A1 | 11/2011 | Abal |
| 2012/0053557 | A1 | 3/2012 | Abal |
| 2012/0078218 | A1 | 3/2012 | Barnes |
| 2012/0083759 | A1 | 4/2012 | Kirkpatrick |
| 2012/0177543 | A1 | 7/2012 | Battrell et al. |
| 2012/0179130 | A1 | 7/2012 | Barnes et al. |
| 2013/0106609 | A1 | 5/2013 | Singh et al. |
| 2013/0267899 | A1 | 10/2013 | Robert et al. |
| 2014/0276424 | A1 | 9/2014 | Davis et al. |
| 2014/0276426 | A1 | 9/2014 | Borges et al. |
| 2014/0276533 | A1 | 9/2014 | Butterfield et al. |
| 2016/0151561 | A1 | 6/2016 | Toro et al. |
| 2017/0032152 | A1 | 2/2017 | Salem et al. |

OTHER PUBLICATIONS

International Search Report and Written Opinion for Application No. PCT/US2015/063002, dated Mar. 8, 2016, 11 pages.
International Search Report and Written Opinion for Application No. PCT/US2015/063007, dated Mar. 8, 2016, 10 pages.
International Search Report and Written Opinion for Application No. PCT/US2015/063010, dated Mar. 8, 2016, 13 pages.
International Search Report and Written Opinion for Application No. PCT/US2015/063013, dated Mar. 8, 2016, 15 pages.
Extended European Search Report for Application No. 15864547.3, dated Aug. 1, 2018, 7 pages.
Extended European Search Report for Application No. 15865327.9, dated Aug. 1, 2018, 7 pages.

* cited by examiner

PUMP CASSETTES WITH PISTON AND INFUSION PUMP SYSTEMS

CROSS-REFERENCE TO RELATED APPLICATION

This application is a continuation-in-part of U.S. patent application Ser. No. 14/557,446, titled "PUMP CASSETTES WITH SLIDER AND INFUSION PUMP SYSTEMS," filed on Dec. 1, 2014, the entire contents of which are hereby incorporated by reference herein for all purposes.

TECHNICAL FIELD

The present disclosure generally relates to apparatus, systems, and methods of delivering medical fluid to patients, and more particularly to infusion pumps, disposable cassettes, and associated methods.

BACKGROUND

Infusion pumps are medical devices that may be used to administer intravenous (IV) fluids. An infusion pump can facilitate the delivery of IV fluids while controlling the volumes and rates for the delivery of such IV fluids. The IV fluids may be delivered at continuous rates or intermittent intervals. Some infusion pumps move fluid through an IV tube using a peristaltic pumping mechanism that acts on the IV tube, while other infusion pumps rely on a cartridge or cassette-like device intended to be manipulated by a pump to cause the IV fluid to flow at the controlled rate or interval. In either case, a typical infusion pump, manipulates the IV tube or IV cartridge such that the IV fluid moves from a container to a patient. The IV tube or IV cartridge is typically connected to or integrated with an IV set (e.g., tubing, valves, and fittings for delivering fluid to a patient), and therefore the cartridge and IV set may be disposable to reduce the risk of infection and contamination.

SUMMARY

Aspects of the subject technology relate to disposable IV pump cassettes and infusion pump systems. In accordance with certain aspects, a pump cassette may comprise a rigid body comprising a frame portion, a base portion, a compliant membrane disposed substantially therebetween, and two opposing longitudinal edge sections, wherein the rigid body comprises a controllable fluid pathway defined in part by the compliant membrane and extending from an inlet port to an outlet port; and a piston disposed at least partially within the rigid body such that movement of the piston varies a volume of a pump chamber defined within the controllable fluid pathway.

In accordance with certain aspects, a pump cassette may comprise therebetween, and two opposing longitudinal edge sections, wherein the rigid body comprises a controllable fluid pathway defined in part by the compliant membrane and extending from an inlet port to an outlet port; a piston disposed at least partially within the rigid body, the piston comprising an actuator-receiving portion; and a slider coupled to the two opposing longitudinal edge sections and longitudinally articulable with respect to the rigid body.

In accordance with certain aspects, an infusion pump system may comprise a processing unit; a cassette recess comprising a circularly moveable actuator mechanism disposed proximate to a back surface of the cassette recess and operably coupled to the processing unit, and a plurality of cassette engagement slots, wherein the cassette recess is adapted to receive a pump cassette comprising: a rigid body comprising a compliant membrane, wherein the rigid body comprises a controllable fluid pathway extending from an inlet port to an outlet port, and a piston disposed at least partially within the rigid body such that movement of the piston varies a volume of a pump chamber defined within the controllable fluid pathway.

It is understood that in accordance with certain aspects, the cassette recess may be integrated into the same box as the processing unit or may be contained in an interface module that may be operatively coupled to the processing unit.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1A:
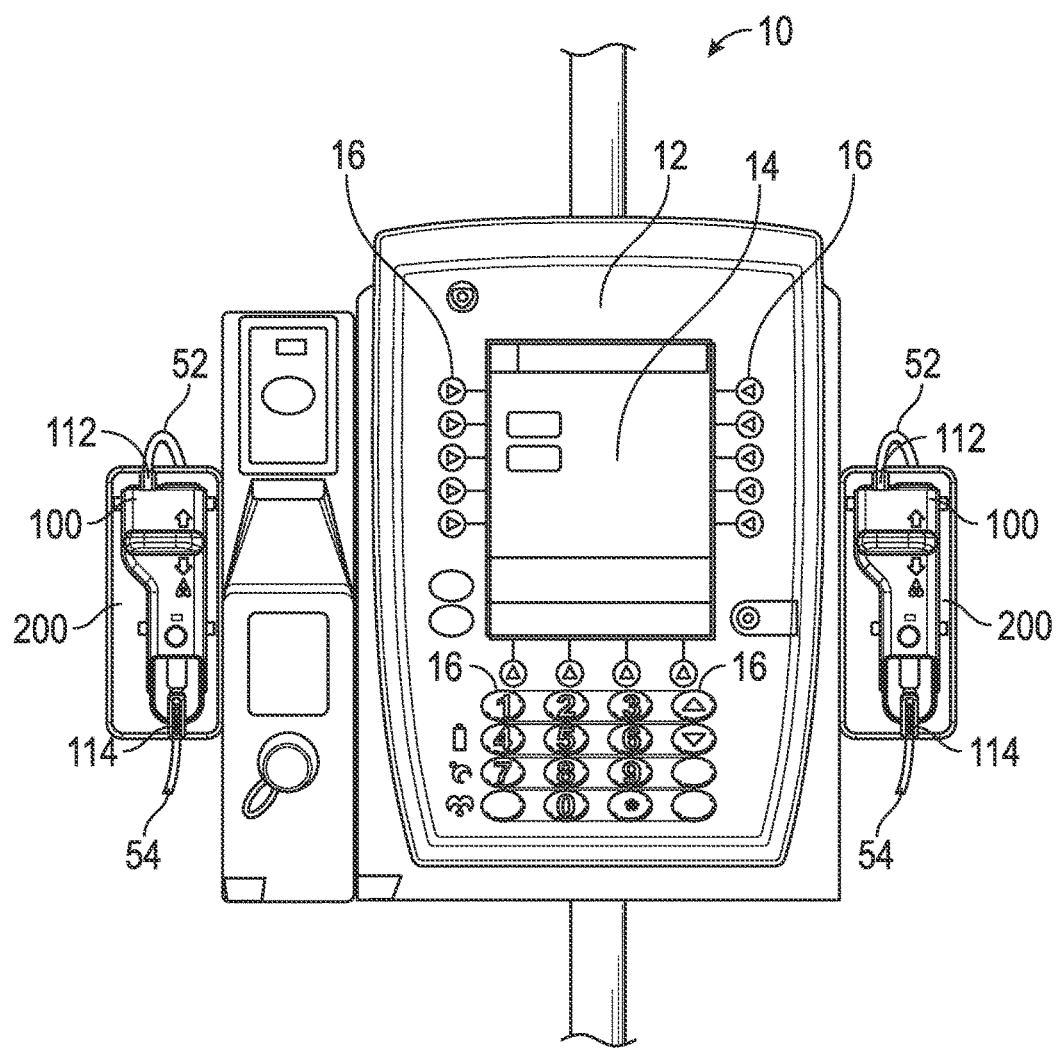
FIGS. 1A and 1B are overview diagrams illustrating examples of infusion pump systems, in accordance with aspects of the present disclosure.

FIG. 1A illustrates an example of an infusion pump system that can contain an embodiment of the piston. It is to be understood that this is only an exemplary infusion pump system, and the piston can be utilized in any type of infusion pump system. The infusion pump system will be generally explained in reference to FIGS. 1-3C. An exemplary infusion pump system 10 may include central processing unit 12 with display screen 14 (e.g., touchscreen display), and data input features 16, for example, a keypad and a series of configurable buttons adjacent to display screen 14. Other types of input and output devices may be used with central processing unit 12 and infusion pump system 10. In certain aspects, central processing unit 12 is operatively coupled to one or more interface modules, with cassette recesses 200, to control and communicate with various operational interfaces thereof.

Figure 1B:
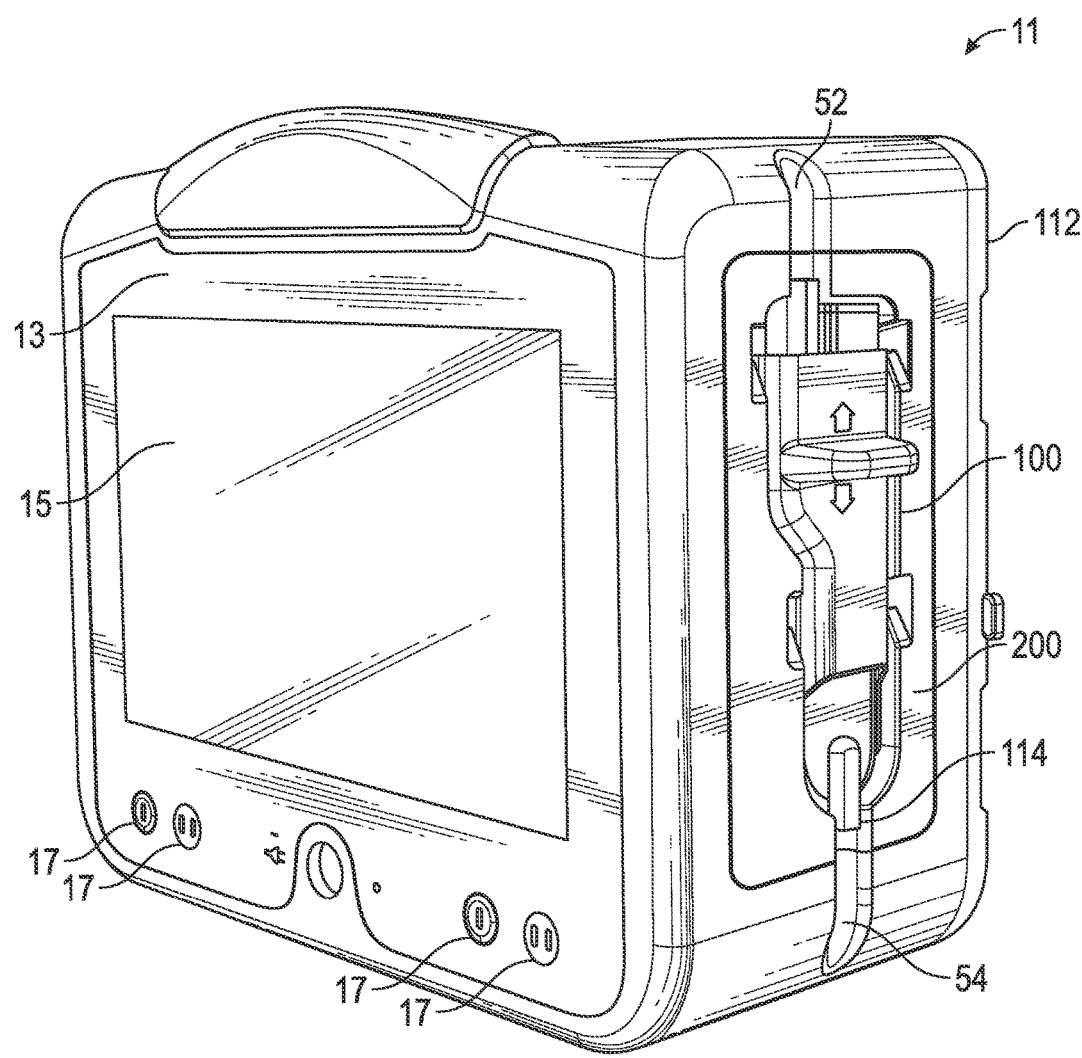

FIG. 1B illustrates another example of an exemplary infusion pump system. This exemplary infusion pump system 11 may include one or more cassette recesses 200 and disposable IV pump cassettes 100. For example, cassette recess 200 may be configured to receive cassette 100 and provide various mechanical couplings and operational interfaces (e.g., fittings, motor, gearing, driveshaft, sensors, etc.).

Infusion pump system 11 may include central processing unit 13 with display screen 15 (e.g., touchscreen display), and data input features 17, for example, a series of configurable buttons adjacent to display screen 15. In some implementations, the display screen 15 may provide a keypad or similar data entry feature. Other types of input and output devices may be used with central processing unit 13 and infusion pump system 11. In certain aspects, central processing unit 13 is operatively coupled to one or more interface modules, with cassette recesses 200, to control and communicate with various operational interfaces thereof.

In operation, an IV bag, syringe or other fluid source 52 may be fluidly connected to inlet 112 of cassette 100, and outlet 114 of cassette 100 may be fluidly connected to a patient 54 as shown in the examples of FIGS. 1A and 1B. Cassettes 100 may comprise a DEHP and Latex-free fluid pathway suitable for various patient populations (e.g., neonate, pediatric, and adult).

In operation, a user (e.g., a caregiver) may obtain a new disposable IV cassette 100 and prime cassette 100 before inserting cassette 100 into cassette recess 200. The caregiver may check for any visible air bubbles in the fluid pathway and may press on any accessible fluid reservoirs (e.g., pressure dome chambers) to move fluid through the cassette 100. Cassette 100 can be securely held and inserted into cassette recess 200 by a single hand of a caregiver. In this regard, caregiver's other hand can be freed to perform other tasks.

Figures 2A, 2B:
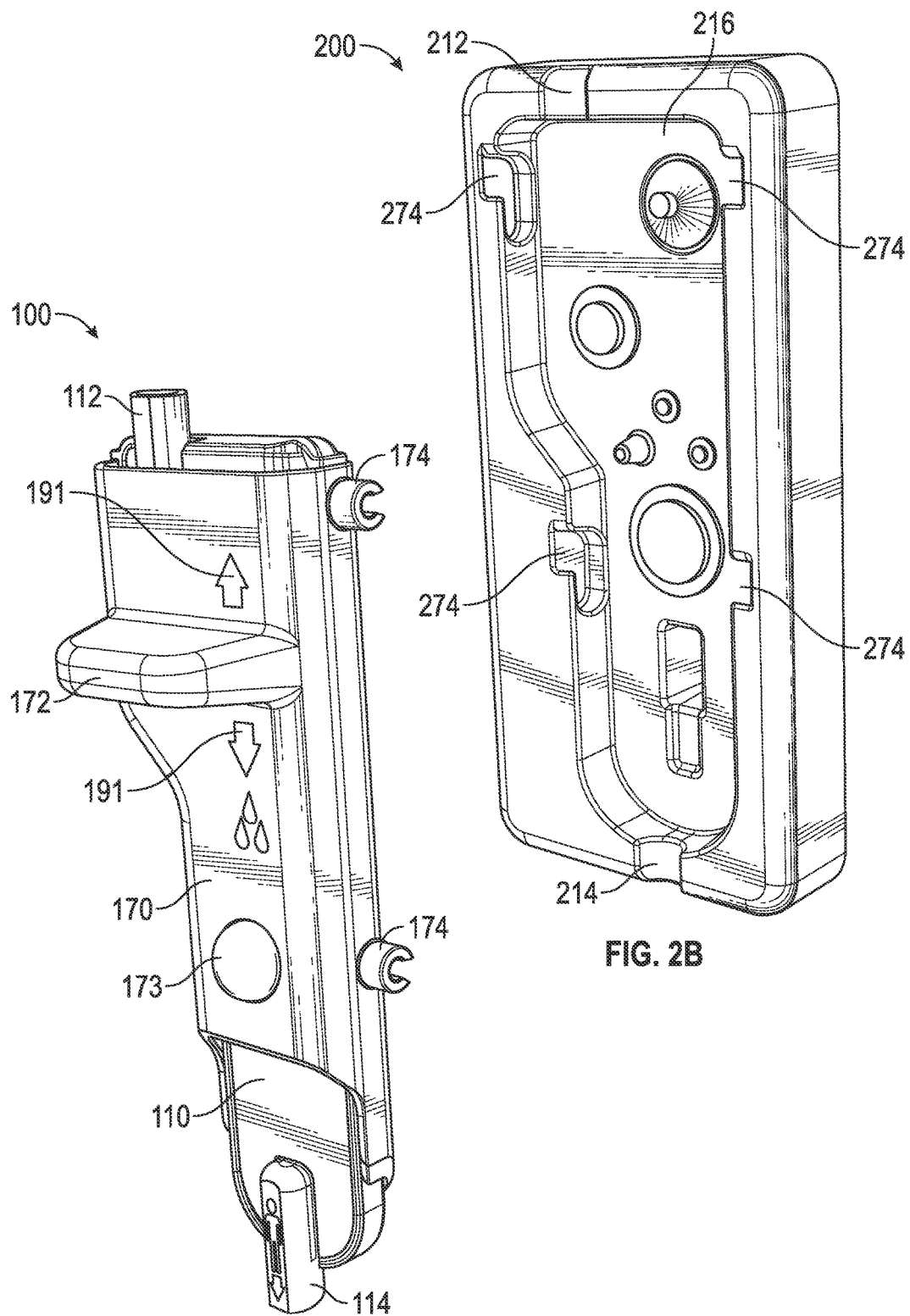
FIGS. 2A and 2B illustrate perspective views of examples of a first embodiment disposable IV pump cassette and cassette recess, in accordance with aspects of the present disclosure.

FIGS. 2A and 2B illustrate examples of a disposable IV pump cassette 100 and corresponding cassette recess 200 of an interface module. Cassette 100 may comprise a cassette body 110 and a slider 170. Cassette 100 may include certain may include certain visual indicators related to operation aspects of the cassette and the infusion pump system in general. For example, cassette may include identifiable images such as fluid drops indicating position of slider 170 for free-flow (flow stop valve 164 in an open position) and a patient figure proximal to outlet 114. In accordance with some aspects, cassette 100 may include lens area 173 for magnification of the fluid pathway within the cassette body 110. Lens area 173 may be disposed on the slider 170 or proximal to outlet 114 and/or an air-in-line detection feature. For example, during priming or prepping a cassette, a user or caregiver may use lens area 173 to ensure that any visible air bubbles have been removed and fluid is flowing properly. In accordance with some aspects, one or more cassette-seated sensors may be disposed within the cassette recess 200 so as to inform central processing unit 12 that the cassette is locked or secured into place within the cassette recess 200 or seat.

Slider 170 can be fixably and slidably engaged with cassette body 110 such that slider 170 may articulate longitudinally 191 with respect to cassette body 110, but will be constrained within range of sliding motion such that the slider remains coupled to the cassette body 110. Slider 170 may be formed from rigid plastic or polymer material having lubricating characteristics (e.g., incorporating silicon or polytetrafluoroethylene (PTFE) additives), and is clear or translucent in accordance with certain embodiments. In some embodiments, slider 170 may be polycarbonate. Slider 170 includes a slider grip 172 or handle portion and a plurality of protrusions 174 or lugs that are configured to be releasably lockable with a plurality of slots 274 of the cassette recess 200 (e.g., L-shaped locking channels). In this regard, cassette 100 can be self-latched into the cassette recess 200. Accordingly, a door or lever action is not required in order to retain the cassette 100 within the cassette recess 200. In an alternative embodiment, an inverse configuration may be desired, in which the cassette recess 200 would contain protrusions or lugs that would be configured to be releasably lockable with a corresponding slots located on the slider or rigid body.

Cassette body 110, or a substantial portion thereof, may extend a depth (D) between 6 mm and 8 mm. Fluid pathway extension member 128 may further extend between 8 mm to 10 mm. In certain aspects, slider grip 172 may extend between 10 mm to 14 mm from cassette body 110. It is to be appreciated that the process of cleaning of inlet recess 212, outlet recess 214, and cassette recess 200 is made efficient in the shallow recess configuration in accordance with certain embodiments should any fluid or debris accumulate within cassette recess 200. The shallow recess configuration of cassette recess 200, and associated longitudinal alignment of cassette 100 such that a smaller of volumetric dimensions of cassette 100 (e.g., depth being smaller than length and width in certain embodiments) further enables additional space for arrangement of mechanical couplings and operational interfaces and optimizes the overall space requirements of cassette recess 200 and infusion pump system in general.

In operation, cassette 100 can be loaded directly into cassette recess 200. In this regard, the direct loading of the cassette 100 will enable avoidance of sheer forces that might otherwise be applied to the sensors, alignment features, and other engaging interfaces of cassette-facing surface 216 of cassette recess 200 from interaction with the interface-facing side of cassette body 110 as it is loaded into cassette recess 200.

Figure 3A:
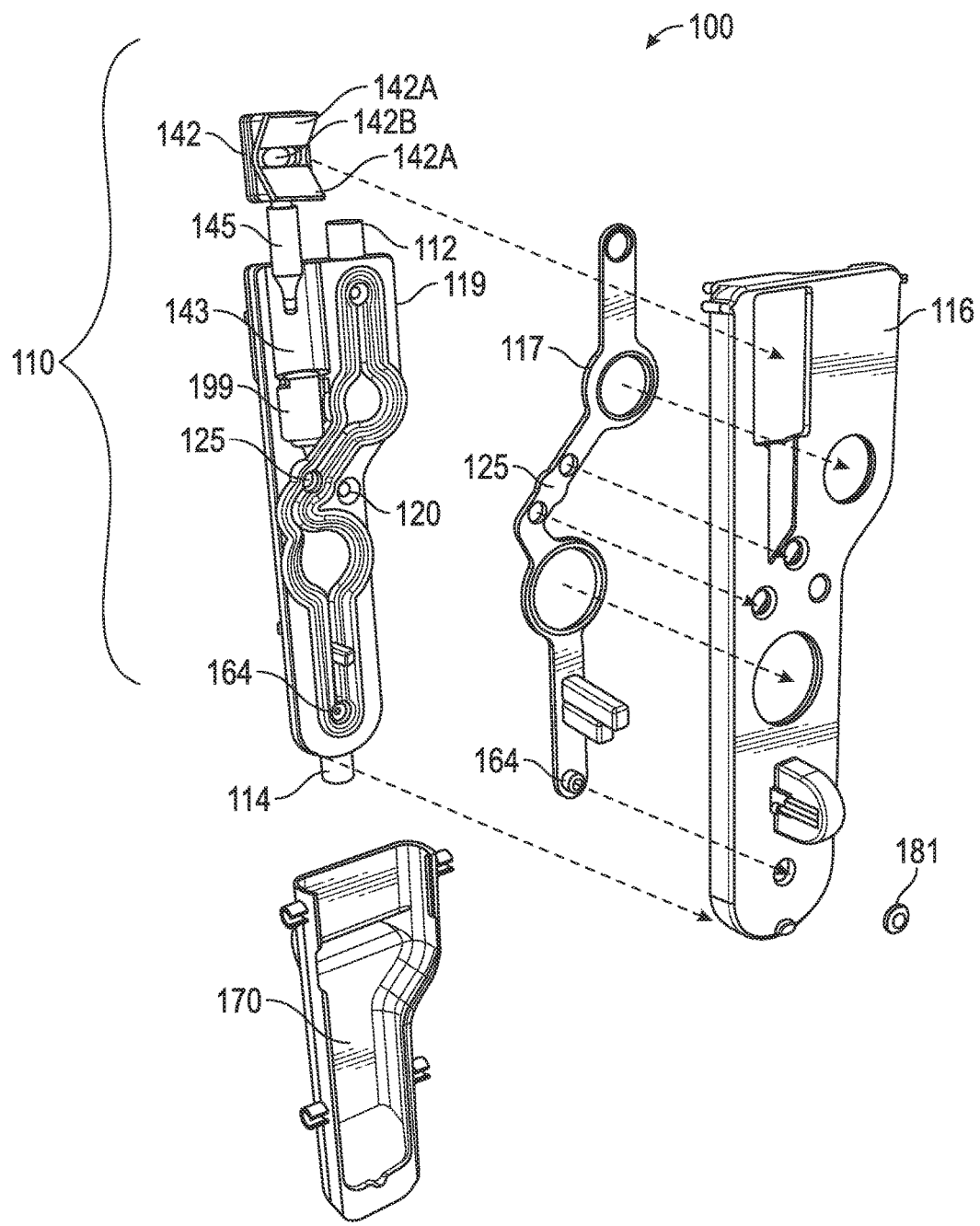
FIG. 3A is an exploded perspective detail view illustrating an example of a first embodiment disposable IV pump cassette, in accordance with aspects of the present disclosure.
Figure 3B:
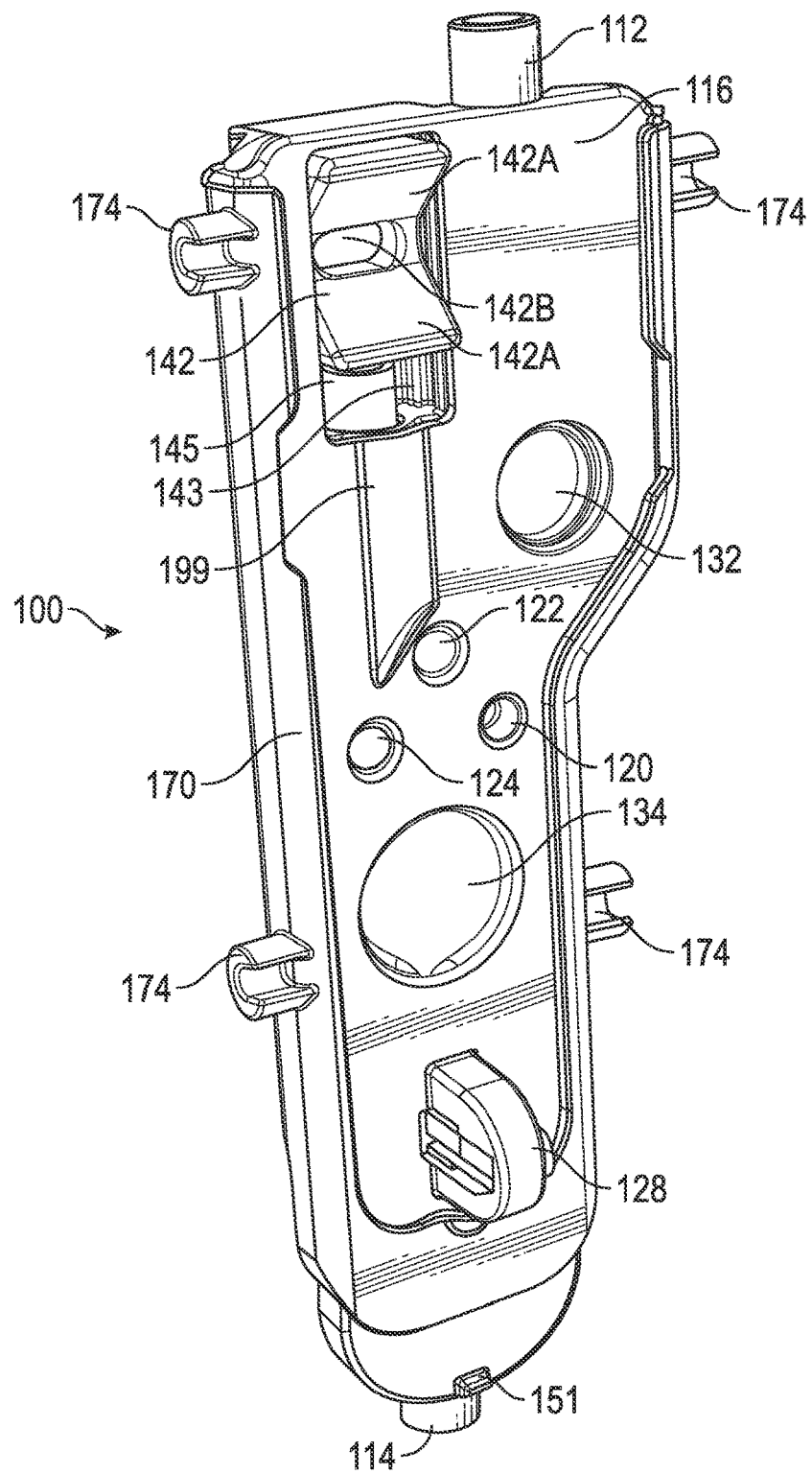
FIG. 3B illustrates a perspective view of an example of a first embodiment disposable IV pump cassette, in accordance with aspects of the present disclosure.

Referring now to the examples of FIGS. 3A and 3B, cassette body 110 may comprise interface-facing frame portion 116 and slider-facing base portion 119 with membrane 117 disposed substantially therebetween (e.g., portions of membrane 117 may extend through some openings of frame portion 116). In accordance with certain embodiments, membrane 117 can be a compliant material co-molded to the frame portion 116 and sealingly engaged with base portion 119 for defining a fluid pathway through cassette body 110 from inlet 112 to outlet 114. Mating edges of frame portion 116 and base portion 119 may be connected by fusing, welding, gluing, or the like. Membrane 117 and base portion 119 may further define a plurality of other features, some of which may be accessed through openings in frame portion 116.

Frame portion 116, membrane 117, and/or base portion 119 may define features in or along the fluid pathway, in accordance with certain embodiments. For example, beginning from inlet 112, the fluid pathway may include features such as, but not limited to, upstream pressure dome 132 (e.g., an inlet-side compliant reservoir), inlet-side valve 122, pump chamber having pump chamber opening/access 125, outlet-side valve 124, downstream pressure dome 134 (e.g., an outlet-side compliant reservoir), fluid pathway extension member 128, and flow stop valve 164. Other features that are not in or along the fluid pathway, but are disposed on cassette body 110, may include positioning port 120 and slider stopper 151. With respect to extension member 128, a portion of the fluid pathway can be extended away or protrude orthogonally from the generally flat and planar exterior surface of interface-facing frame portion 116 so as to make the fluid in the fluid pathway available for certain detection techniques performed by infusion pump system 10, 11 as further explained below. As illustrated in the example of FIGS. 3A and 3B, fluid pathway extension member 128 may be formed from orthogonally extending portions of frame portion 116, membrane 117, and/or base portion 119.

In accordance with certain embodiments, membrane 117 may be formed from a thermoplastic elastomer (TPE). Characteristics of certain TPEs can enable effective co-molding with other materials, for example, polycarbonate. Accordingly, in some embodiments, membrane 117 may be co-molded to frame portion 116 and striker 181 may be co-molded to a portion of membrane 117 defining a flow stop valve 164. However, in some embodiments, membrane 117 can be formed from silicon, a silicon-based compound, an elastomeric material suitably compliant for fluid flow, or the like.

In accordance with certain embodiments, interface-facing frame portion 116 and slider-facing base portion 119 may be formed from a rigid plastic such as, but not limited, a polycarbonate. Additionally, the rigid plastic of frame portion 116 and base portion 119 may be clear or translucent. The material of membrane 117 (e.g., TPE or other compliant material) and rigid plastic slider 170 may also be clear or translucent, thereby allowing a user or caregiver to readily observe fluid passage through a substantial portion of the fluid pathway of cassette body 110. In some embodiments, the fluid pathway portion of cassette body 110 will be clear or translucent, and other portions will be frosted so as to direct a user or caregiver's attention to the fluid pathway.

In some implementations, slider 170, base portion 119, and membrane 117 may be clear or translucent (or at least some portions along the fluid pathway), and the frame portion 116 may not be translucent. For example, the frame portion 116 may be colored in a manner so as to contrast against a color or tint of the fluid expected to be used with cassette 100. In some embodiments, a lens area 173 may be disposed on base portion 119 alternatively, or in addition to, lens area 173 disposed on slider 170.

Figure 3C:
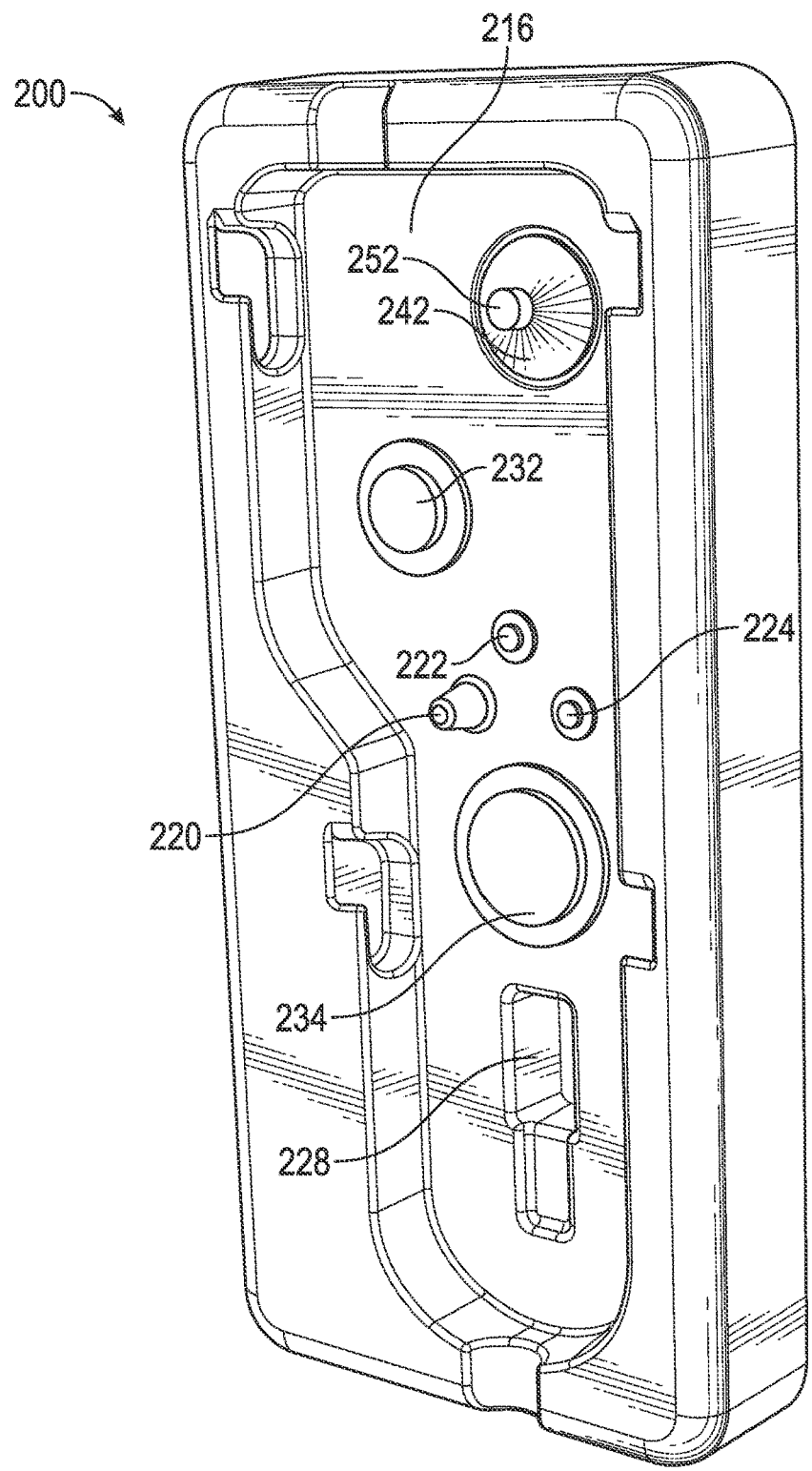
FIG. 3C illustrates a perspective view of an example of a first embodiment cassette recess, in accordance with aspects of the present disclosure.

As illustrated in the examples of FIG. 3A-3C, cassette body 110 may include a pump drive assembly in accordance with certain embodiments. For example, the pump drive assembly may include pump drive interface 142 for receiving pump actuator 242 of cassette recess 200. Pump drive interface 142 can be operatively coupled to piston 145 slidably engaged within piston guide 143 and/or casing 199 (e.g., a generally cylindrical and/or frustoconical piston barrel) such that reciprocal movement of piston 145 within a pump chamber formed in part by the piston barrel 199 provides a moving seal that defines the edge of the pump chamber to urge fluid through the fluid pathway of cassette body 110. In this regard, the pump chamber may be defined by a portion of the piston guide 143 or casing 199 distal from the pump drive interface 142 that is adjacent to and fluidly coupled with a tract or section of the fluid pathway between inlet-side valve 122 and outlet-side valve 124. Thus, the reciprocal motion of the piston 145 along piston guide 143 and within piston barrel 199 is such that a volume of the pump chamber may be varied by movement of the piston 145 in accordance with certain embodiments. In accordance with certain aspects, piston 145 resides and moves within a rigid bore and provides a seal that permits fluid to be drawn into the pump chamber via pump chamber opening/access 125 on the fill cycle and expelled on the delivery cycle.

Figure 5A:
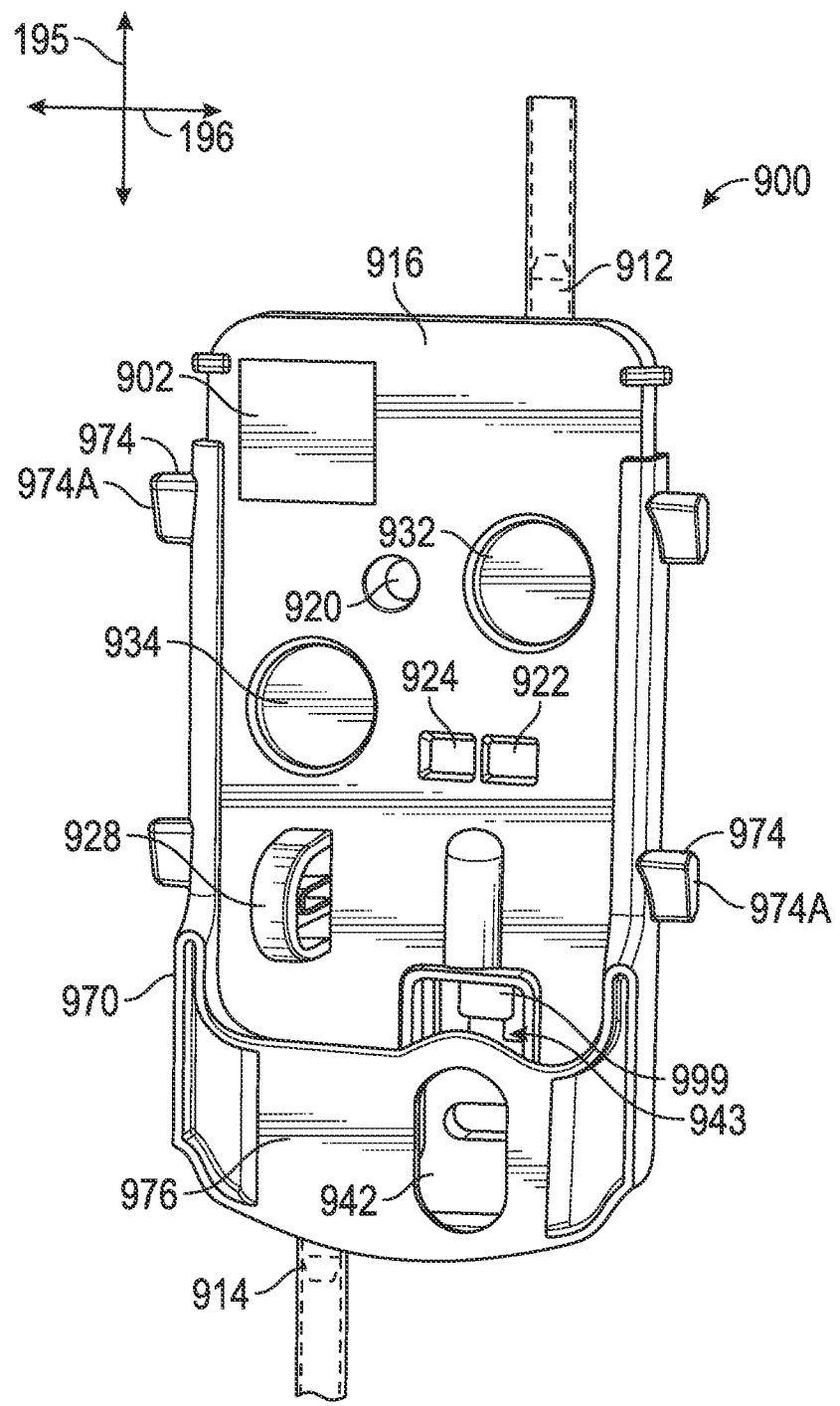
FIG. 5A illustrates a perspective view of the example embodiment of the disposable IV pump cassette of FIGS. 4A and 4B, in accordance with aspects of the present disclosure.
Figure 5B:
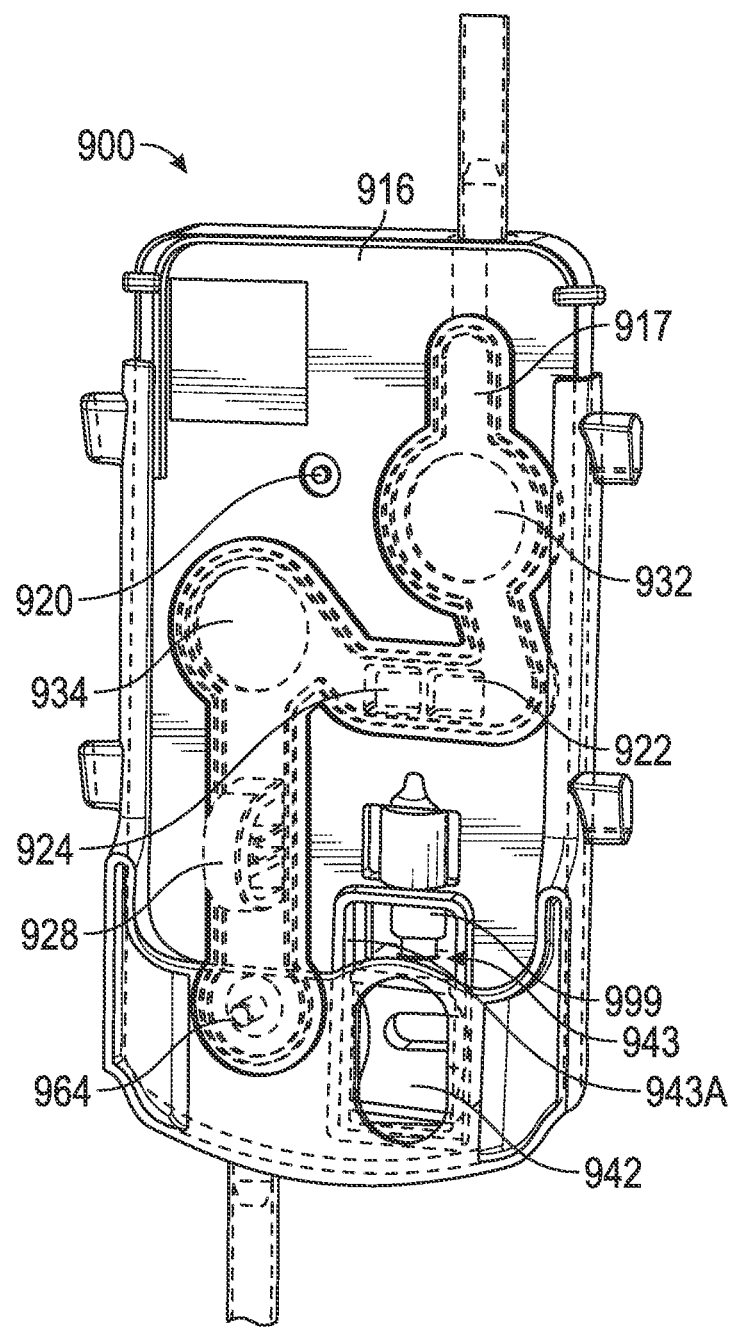
FIG. 5B illustrates another perspective view of the example embodiment of the disposable IV pump cassette of FIG. 5A, in accordance with aspects of the present disclosure.

Piston 145 may include one or more circumferential seals as described hereinafter in connection with (for example) FIGS. 5F and 5G. The one or more seals of the piston 145 may be slidable seals that are fixed to the piston and contact and slide along an internal wall of piston barrel 199 to form a movable barrier of the pump chamber. In some embodiments, an additional wiper seal (not shown) may be positioned within or proximal to piston barrel 199 (e.g., integrally formed on or attached to a sidewall surface of piston barrel 199) and slidably engaged with a surface of piston 145 thereby reducing the possibility of any substances (e.g., dirt, dried fluid particles, airborne pathogens, etc.) near the cassette 100 from contacting the one or more slidable seals of the piston 145.

Additionally, piston 145 may include a reduced tip portion for more precise volumetric displacement of fluid into and out of pump chamber through pump chamber opening/access 125. The reduced tip portion may have a shape that corresponds to a shape of the pump chamber to reduce air accumulation in the pump chamber by forcing air out of the pump chamber into the fluid path rather than accumulating in the piston barrel. In some embodiments, the nose or tip of the piston 145 is substantially aligned with a bottom of the fluid pathway to eliminate any dead space (e.g., internal space where air may accumulate) in the pump chamber as well as reduce any drag associated with the fluid flow through the fluid pathway. Thus, in some embodiments, the dead space is less than 1% of the total volume of the pump chamber.

For example, a pumping operation of infusion pump system 10, 11 when cassette 100 is primed and seated in cassette recess 200 may comprise activating outlet-side valve actuator 224 such that outlet-side valve 124 is closed or sealed while activating inlet-side valve actuator 222 such that inlet-side valve 122 is opened. Opening of inlet-side valve 122 may coincide with or occur shortly before the start of a reverse stroke of piston 145 (e.g., a movement of piston 145 away from pump chamber). Accordingly, fluid can flow from upstream pressure dome 132 to the pump chamber. Alternatively, or in addition to, outlet-side valve 124 may comprise a one-way valve mechanism that permits flow of fluid under normal conditions in one direction (from a fluid container to a patient). Additionally, in some alternative embodiments, inlet-side valve 122 may also comprise a one-way valve or choke mechanism permitting flow of fluid in primarily one direction (e.g., from a fluid container to a patient) under normal operating conditions. In this configuration, cassette recess 200 may not need to incorporate either outlet-side valve actuator 224 or inlet-side valve actuator 222. Outlet-side valve 124 and inlet-side valve 122 may limit flow of fluid in one direction, but permit flow in an opposite direction in the event fluid pressure overcomes a cracking pressure of the valves.

Continuing with the valve-operated implementation, pumping operation may comprise activating outlet-side valve actuator 224 such that outlet-side valve 124 is open while activating inlet-side valve actuator 222 such that inlet-side valve 122 is closed or sealed. Opening of outlet-side valve 124 may coincide with or occur shortly before a start of a forward stroke of piston 145 (e.g., a movement of piston 145 toward the opening/access 125 of the pump chamber such that the volume of the pump chamber is reduced). Thus, fluid can flow from pump chamber down the fluid pathway to outlet 114.

In certain embodiments, the upstream pressure dome 132 may be smaller than the downstream pressure dome 134 to minimize retained volume. Likewise, the downstream pressure dome 134 may be larger than the upstream pressure dome 132 to improve resolution of fluid pressure thereby allowing for an accurate and precise volume of fluid to be pumped and any upstream or downstream pressures to be accurately measured.

Referring to FIGS. 3A-3C, pump drive interface 142 and pump actuator 242 may be configured as a reciprocating motion mechanism (e.g., a scotch-yoke configuration, a cam-driven (perpendicular motion) configuration, a linear actuator, a rotary actuator, etc.) in certain implementations. In such implementations, pump drive interface 142 may include opposing ramp portions 142A for guiding a rotatable pin 252 of pump actuator 242 toward a slot such as elongate slot 142B of pump drive interface 142. The opposing ramp portions may allow self-alignment of the piston 145 (e.g., the slot 142B) to the pump interface pin 252. For example, the outer edges of the opposing ramp portions 142A may be arranged at a distance that will ensure engagement with the rotatable pin 252 of pump actuator 242. When the rotatable pin 252 contacts one of the ramp portions 142A, the pump drive interface 142 will move the piston to align the elongate slot 142B of pump drive interface 142 with the rotatable pin 252 of pump actuator 242. However, it is to be appreciated that other pump drive assemblies are contemplated with cassette 100 and cassette recess 200 in accordance with the present disclosure.

In the example of FIGS. 3A-3C, piston 145 may be driven by a force provided by pin 252 against the sidewall surfaces of elongate slot 142B as pump actuator 242 rotates. The elongated configuration of slot 142B may allow pin 252 to reciprocate back and forth along the elongated dimension of the slot without providing a force on piston 145 in that direction as the pin provides a perpendicular force for actuating piston 145 within piston barrel 199. However, other configurations of slot 142B may be provided to generate various pumping characteristics with a rotating pin 252.

In some embodiments, pump drive assembly may be configured to produce a 3.5 mm piston stroke for operation with a pump chamber configured to be a 10 mm outer diameter reservoir. Moreover, the pump drive assembly may be arranged below the pump chamber, in accordance with some embodiments.

Figure 4A:
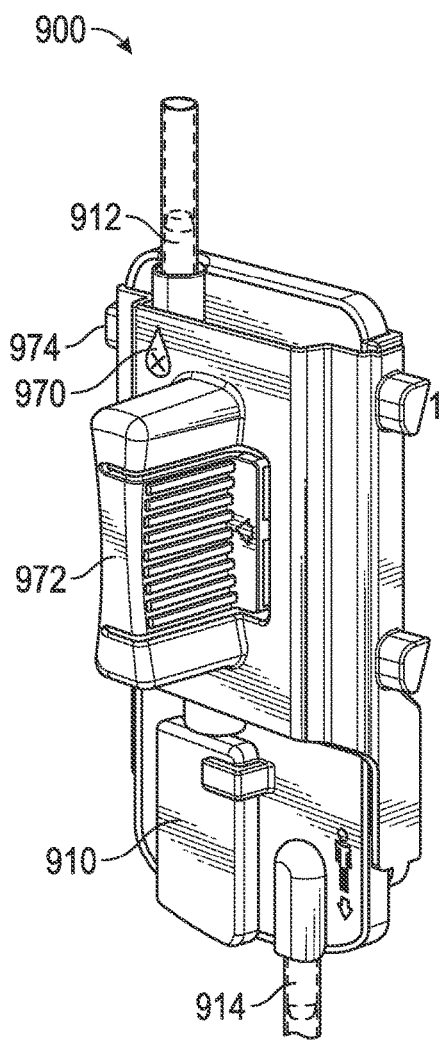
FIGS. 4A and 4B illustrate perspective views of examples of another embodiment of a disposable IV pump cassette and cassette recess, in accordance with aspects of the present disclosure.
Figure 4B:
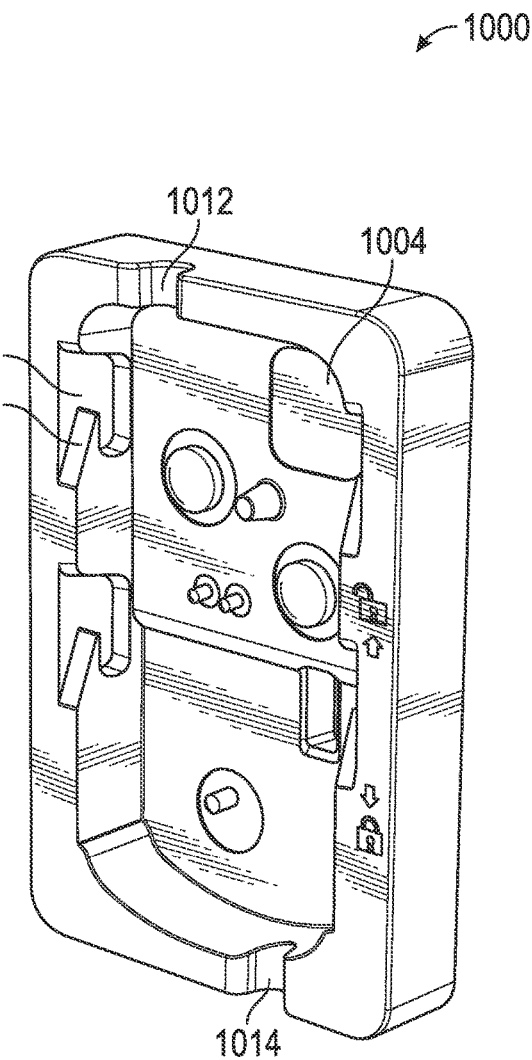

In certain embodiments, cassette recess 200 may include an upstream pressure sensing probe 232 and downstream pressure sensing probe 234 enabling measurement of in-line pressure and fault isolation to a section of the fluid pathway. For example, upstream pressure sensing probe 232 may operably contact upstream pressure dome 132 through a corresponding opening of interface-facing frame portion 116. Similarly, downstream pressure sensing probe 234 may operably contact downstream pressure dome 134 through a corresponding opening of frame portion 116. FIGS. 4A and 4B illustrate examples of a disposable IV pump cassette 900 and corresponding cassette recess 1000 of an interface module. In accordance with certain embodiments, cassette 900 may comprise a cassette body 910 and a slider 970. Cassette 900 may include certain may include certain visual indicators related to operation aspects of the cassette and the infusion pump system in general. For example, cassette may include identifiable images such as fluid drops indicating position of slider 970 for free-flow (e.g., flow stop valve 964 in an open position) and a patient figure proximal to outlet 914. In accordance with some aspects, one or more cassette-seated sensors may be disposed within the cassette recess 1000 so as to inform central processing unit 12 that the cassette is locked or secured into place within the cassette recess 1000 or seat. For example, cassette recess may include a window 1004 (or aperture) such that cassette identifier 902 (FIG. 5A) can be scanned. Cassette identifier 902 may include various information such as, but not limited to, a manufacturer, type, and use parameters of cassette 900.

Moreover, cassette identifier 902 may be disposed on a top half of the exterior surface of interface-facing frame portion 916 with respect to gravity during use. Thus, a bottom half of the exterior surface of interface-facing frame portion 916 can be reserved for pump drive assembly and flow stop valve features, in accordance with certain embodiments.

Slider 970 can be fixably and slidably engaged with cassette body 910 such that slider 970 may articulate longitudinally with respect to cassette body 910, but will be constrained within range of sliding motion such that the slider remains coupled to the cassette body 910. Slider 970 may be formed from rigid plastic or polymer material having lubricating characteristics (e.g., incorporating silicon or polytetrafluoroethylene (PTFE) additives), and is clear or translucent in accordance with certain embodiments. In some embodiments, slider 970 may be polycarbonate. In accordance with certain aspects, slider 970 may be lockable at one or more positions, and may include a slider grip 972 for unlocking and articulating slider 970. Slider 970 may also include a plurality of protrusion 974 or lugs that are configured to mate and be releasably lockable with a plurality of slots 1074 of the cassette recess 1000 (e.g., L-shaped locking channels).

Each of the plurality of protrusions 974 may also comprise a flat face portion 974a that is configured to interface with a respective flat face ramp portions 1074a of the cassette engagement slots 1074. In this regard, cassette 900 can be self-guided and self-latched into the cassette recess 1000. Accordingly, a door or lever action is not required in order to retain the cassette 900 within the cassette recess 1000.

Additionally, an overall size of cassette 900 and cassette recess 1000 may be reduced, in accordance with some aspects. For example, in certain embodiments, cassette body 910 may extended longitudinally a length between 70 mm and 90 mm. For orientation reference with respect to the various views of the examples illustrated of FIGS. 4A and 4B, longitudinal axis or y-axis 195 and latitudinal axis or x-axis 196 are provided as a reference on certain figures (e.g., FIG. 5A).

Various types, placement, and orientations of the plurality of protrusions 974 disposed on slider 970 are contemplated in the present disclosure. Aspects of the various cassette-coupling techniques illustrated in the example cassette embodiments described herein may be further combined and arranged into additional configurations suitable for specific implementations given the benefit of the present disclosure.

Cassette body 910 may comprise interface-facing frame portion 916 and slider-facing base portion 919 (FIGS. 5A and 5B) with membrane 917 disposed substantially therebetween. Portions of membrane 917 may extend through or be accessible from some openings of frame portion 916 (e.g., upstream pressure dome 932, downstream pressure dome 934, inlet-side valve 922, and outlet-side valve 924). In accordance with certain embodiments, membrane 917 can be a compliant material co-molded to the frame portion 916 and sealingly engaged with base portion 919 for defining a fluid pathway through cassette body 910 from inlet 912 to outlet 914. Mating edges of frame portion 916 and base portion 919 may be connected by fusing, welding, gluing, or the like. Membrane 917 and base portion 919 may further define a plurality of other features, some of which may be accessed through openings in frame portion 916.

Frame portion 916, membrane 917, and/or base portion 919 may define features in or along the fluid pathway, in accordance with certain embodiments. For example, beginning from inlet 912, the fluid pathway may include features such as, but not limited to, upstream pressure dome 932 (e.g., an inlet-side compliant reservoir), inlet-side valve 922, pump chamber 925, outlet-side valve 924, downstream pressure dome 934 (e.g., an outlet-side compliant reservoir), fluid pathway extension member 928, and flow stop valve 964. Other features that are not in or along the fluid pathway, but are disposed on cassette body 910, may include positioning port 920 and slider stopper 951.

Figure 5C:
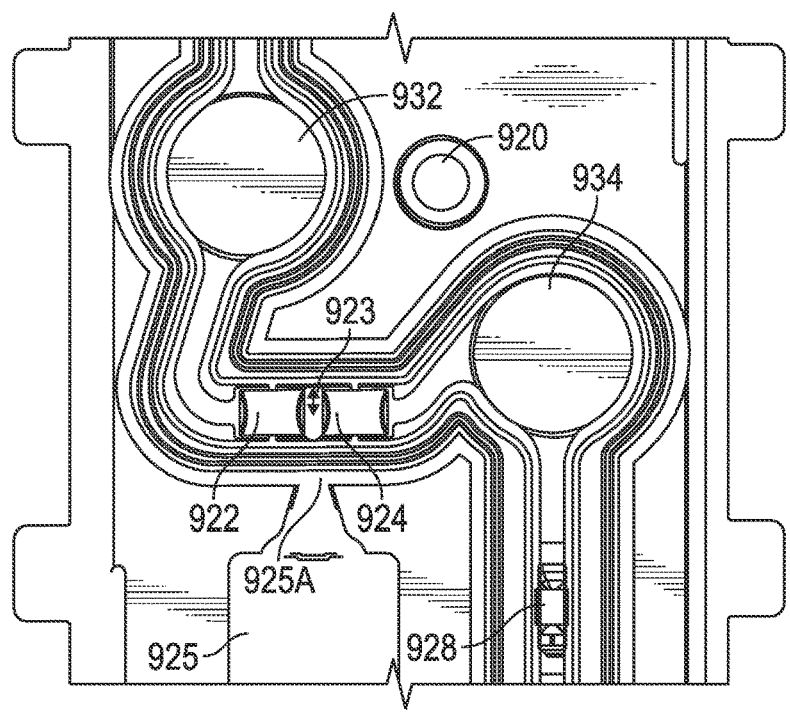
FIG. 5C illustrates an enlarged cross-sectional perspective view of the example embodiment of the disposable IV pump cassette of FIG. 5B, in accordance with aspects of the present disclosure.
Figure 5D:
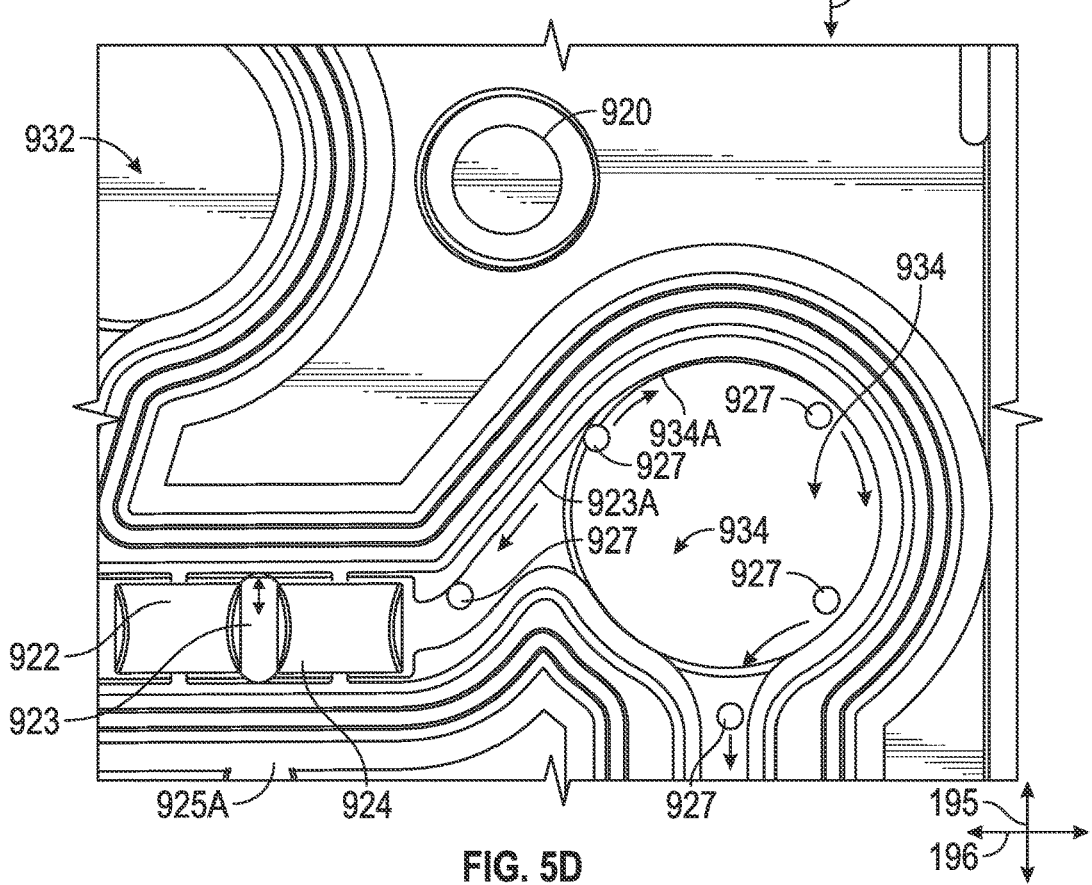
FIG. 5D illustrates a further enlarged cross-sectional perspective view of the example embodiment of the disposable IV pump cassette of FIG. 5C, in accordance with aspects of the present disclosure.
Figure 5E:
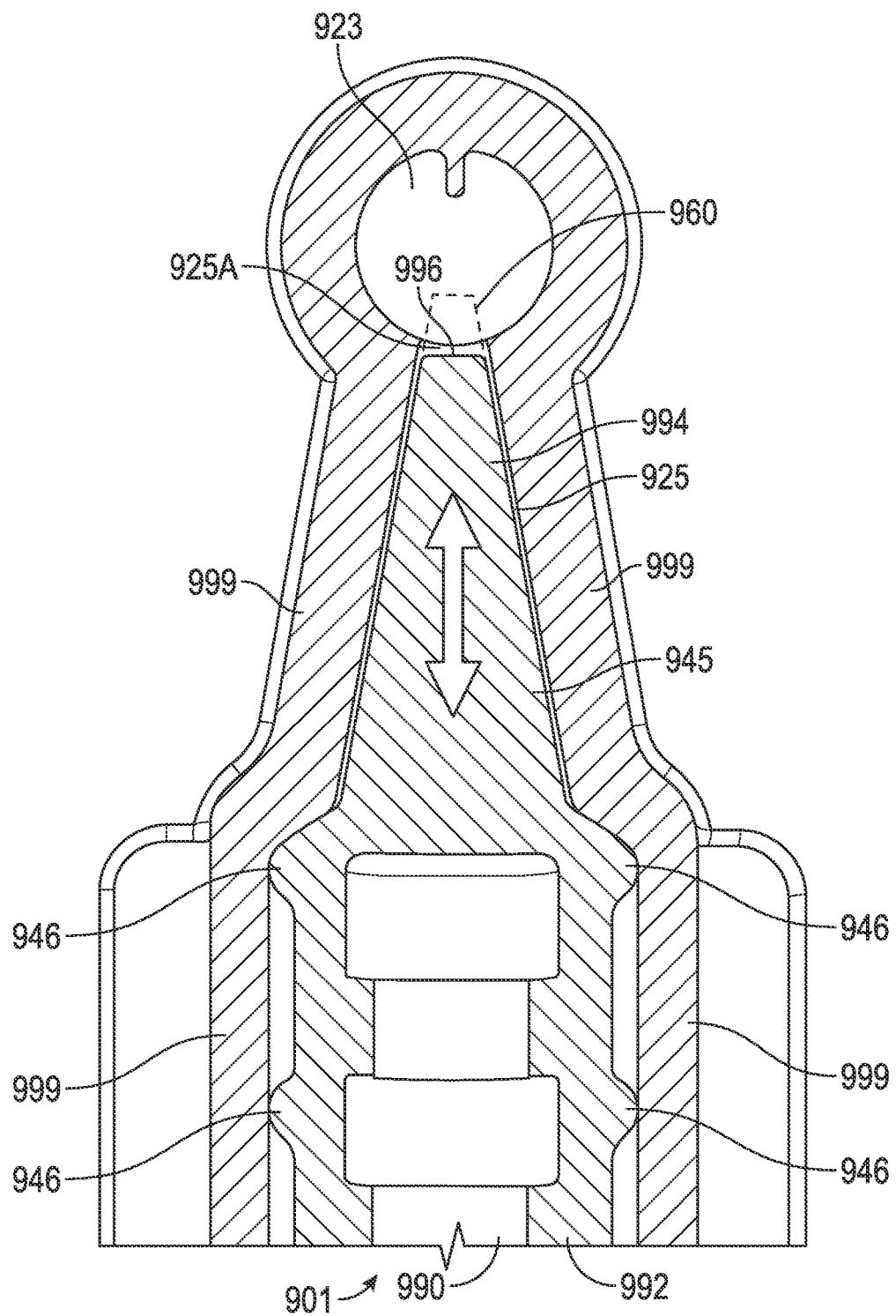
FIG. 5E illustrates another enlarged cross-sectional perspective view of the example embodiment of the disposable IV pump cassette of FIG. 5C, in accordance with aspects of the present disclosure.
Figure 5F:
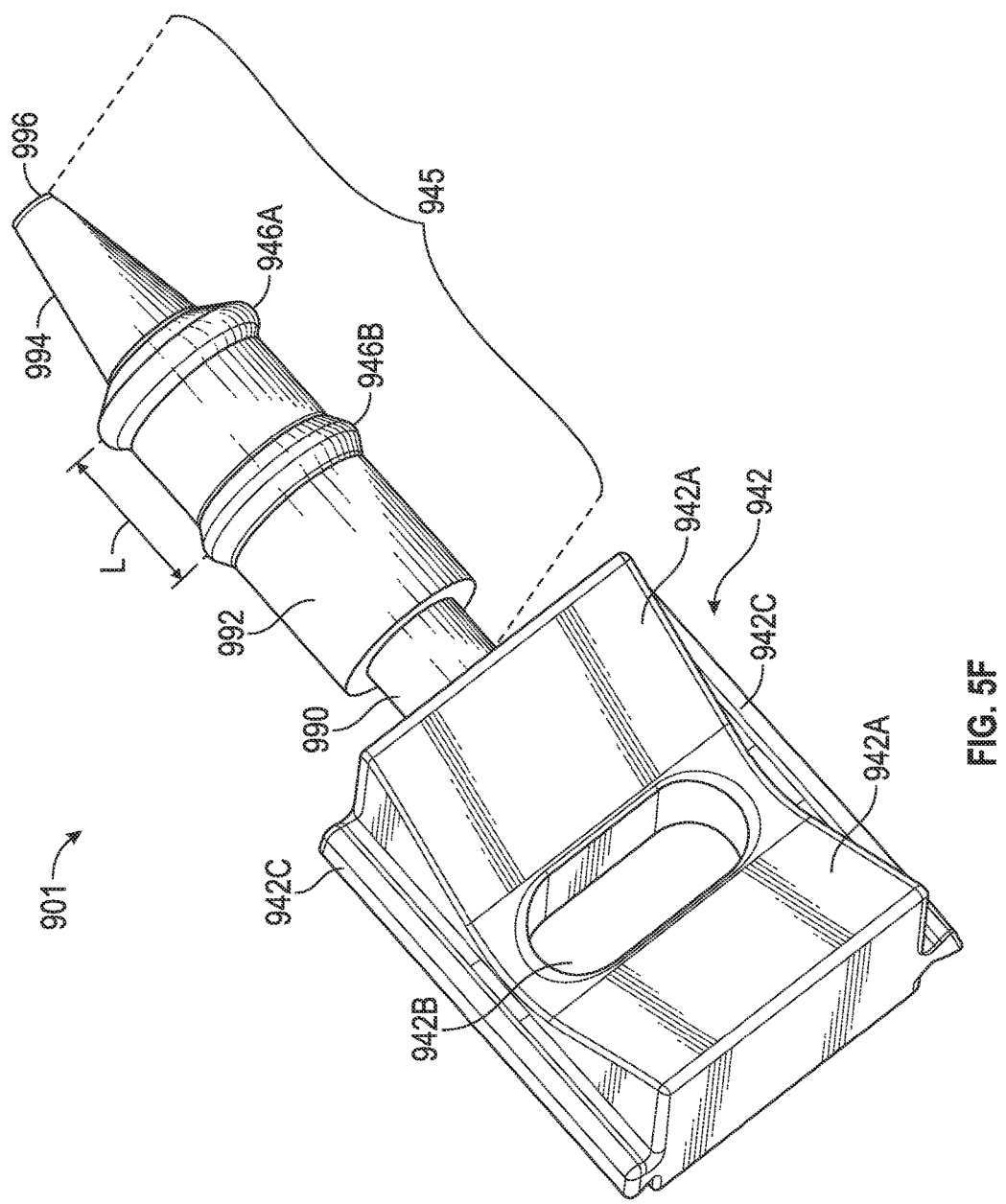
FIG. 5F illustrates a perspective view of an example of an embodiment of a piston of a disposable IV pump cassette, in accordance with aspects of the present disclosure.

FIGS. 5C-5E are enlarged, longitudinal cross-sectional views of cassette body 910 proximate to pump chamber 925. Opening 925a of the pump chamber 925 (e.g., when piston head portion 945 is retracted) is disposed between the inlet-side valve 922 and outlet-side valve 924 along a bottom the fluid pathway section 923. In some embodiments, the nose or tip 996 of the piston head portion 945 is substantially aligned with a bottom of fluid pathway section 923 (FIG. 5E) to eliminate any dead space (e.g., internal space where air may accumulate) in pump chamber 925 as well as reduce any drag associated with the fluid flow through the fluid pathway section 923. Thus, in some embodiments, the dead space is less than 1% of the total volume of the pump chamber 925. For example, in certain embodiments, the volume of the pump chamber is 80 microliters when the piston head portion 945 is fully retracted in its reciprocating cycle.

As indicated by dashed line 960 (FIG. 5E), in some embodiments, the nose or tip of the piston head portion 945 may optionally be configured to extend, in a forward-most position, into the fluid pathway 923. A piston head portion having a nose or tip that extends into the fluid pathway may increase the amount of air that is pushed out of the pump chamber in a pumping cycle.

In this regard, it can be advantageous to place the inlet-side valve 922 and outlet-side valve 924 close together along the fluid pathway section 923 proximal to the pump chamber 925. For example, a distance between the inlet-side valve 922 and outlet-side valve 924 is approximately between 4 millimeters and 7 millimeters in some embodiments. It is to be appreciated that piston pump techniques can provide repeatedly precise positive displacement of fluid in the pump chamber 925.

In accordance with certain embodiments, a section or tract of the fluid pathway leading from the area of the outlet-side valve 924 may comprise a straight edge portion 923a that is tangent to an arcuate edge 934a of the downstream pressure dome 934. The tangentially aligned straight edge 923a and arcuate edge 934a are top edge portions with respect to an orientation of the cassette 900 with respect to gravity, for example, as the cassette 900 would be installed into cassette recess 1000 such that longitudinal axis or y-axis 195 is substantially aligned with gravity.

With respect to the orientation of pump chamber 925 of cassette 900 and a pump chamber having pump chamber opening/access 125 of cassette 100, in certain embodiments, it may be advantageous to have pump chamber 925 in order to prevent or limit the impact of air bubbles in pump chamber accuracy. For example, in a pump chamber having pump chamber opening/access 125 during the delivery phase of the pump cycle, fluid will be expelled first and any air that accumulates in the pump chamber of cassette 100 and between the inlet-side valve 122, outlet-side valve 124 will remain thereby decreasing pumping accuracy of the system. In contrast, pump chamber 925 of cassette 900 will first expel any air that is in the pump chamber, thereby preventing air from accumulating in the pump chamber 925 and in the region between the inlet-side valve 922, outlet-side valve 924 and maintaining accuracy. For example, with additional reference to the example of FIG. 5I, one or more fluid sensors may be disposed within sensor slot 1028. The one or more fluid sensors disposed within sensor slot 1028 can be ultrasonic sensors configured as an air-in-line detector, for example. In certain embodiments, extension member 928 may be disposed on cassette body 910 and positioned along the fluid pathway between downstream pressure dome 934 and flow stop valve 964. However, in some embodiments, extension member 928 can be positioned at other locations along the fluid pathway such as, but not limited to, between inlet 912 and upstream pressure dome 932. Additionally, in other embodiments, a plurality of extension members 928 with a plurality of corresponding sensor slots 228 may be positioned along a fluid pathway of cassette body 910.

With reference to the examples illustrated in FIGS. 5A-5I, cassette body 910 may include a piston 901 as a pump drive assembly in accordance with certain embodiments. The piston 901 may be longitudinally moveable with respect to the rigid body of pump cassette 900. For example, the piston 901 may include an actuator-receiving portion 942 as a pump drive mechanism for receiving pump actuator 1042 of cassette recess 1000. Actuator-receiving portion 942 may include opposing ramp portions 942a and an elongate slot 942b. In certain embodiments, elongate slot 942b may be arranged orthogonal to a direction of movement of the piston. Actuator-receiving portion 942 can be operatively coupled to piston head portion 945 slidably positioned or engaged within piston guide 943 or casing 999 (e.g., a generally cylindrical or frustoconical casing) such that reciprocal movement of piston head portion 945 may urge fluid into and out of the pump chamber 925 and through the fluid pathway of cassette body 910. The piston guide 943 or other portions of the frame portion 916 and/or base portion 919 may include guideslots 943a (e.g., see FIGS. 5B and 5F) that are received by guiderails 942c on the actuator-receiving portion 942 for prohibiting rotational movement of the piston within the rigid body.

The pump chamber 925 may be defined by a portion of the piston guide 943 or casing 999 distal from the actuator-receiving portion 942 that is adjacent to and fluidly coupled with a tract or section of the fluid pathway between inlet-side valve 922 and outlet-side valve 924. Piston head portion 945 may comprise one or more slideable seals 946. Based on the stroke of the piston and the position of the innermost seal 946 along the piston's path as piston head 945 moves, the innermost seal 946 may define the boundary of a changeable volume portion of the pump chamber during reciprocal movement of piston head portion 945 slidably disposed within the piston barrel 999. For example, piston head portion 945 may comprise a first seal 946a proximal to a tip end of the piston head portion 945. The first seal 946a can provide a sealed movable barrier of the pump chamber 925. Piston head portion 945 may also comprise a second seal 946b distal from the tip end with respect to the first seal 946a. The second seal 946b can provide a sealed movable exterior-facing barrier that prevents any substances (e.g., dirt, dried fluid particles or pathogens (airborne or not), or any other substance, particle, or microorganism) near the cassette 900 from contacting the first seal 946a. In this way, such substances can be prevented from direct contact with the first seal 946a that may compromise the sealed movable barrier of the pump chamber 925. In certain embodiments, the first seal 946a is disposed on sealing member 992 at a specific distance L from the second seal 946b such that the path of second seal 946b within piston barrel 999 does not overlap the path of seal 946a in the piston barrel. For example, the distance L may be longer than the stroke of the piston so that seal 946a does not contact any portion of the surface of the piston barrel that is contacted by seal 946b. In this way, seal 946a may be prevented from contacting any debris (e.g., dirt, dried fluid particles or pathogens (airborne or not), or any other substance, particle, or microorganism) from seal 946b. In certain embodiments, the first seal 946a and the second seal 946b are circumferential as shown in FIGS. 5E-5G.

The volume in pump chamber 925 changes with the reciprocal motion of the piston head portion 945 such that a volume of the pump chamber 925 may be varied by movement of the piston head portion 945 in accordance with certain embodiments.

As shown in FIG. 5E, piston head portion 945 may include a center post 990 and a sealing member 992. Sealing member 992 may be integrally formed on center post 990 (e.g., by forming center post 990 and sealing member 992 from a common material in an injection molding process or from different materials in a two-shot injection molding process) or sealing member 992 may be formed separately from center post 990 and may be configured to be installed onto center post 990 (e.g., by pressing or snapping sealing member 992 onto center post 990). In accordance with an embodiment, center post 990 may extend from and be integrally formed with actuator-receiving portion 942. Sealing member 992 may be formed from the same material as center post 990 or from a different material. For example, sealing member 992 may be formed from a relatively softer material such as a silicon-based material that facilitates forming a slidable seal between each of seals 946 and the interior wall of a pump chamber such as pump chamber 925. Seals 946 of piston head portion 945 may be integrally formed portions of sealing member 992 (e.g., circumferential protrusions extending around the cylindrical or conical circumference of member 992).

The one or more slideable seals 946 of the piston head portion 945 may contact an internal wall of piston barrel 999 to form a movable barrier of the pump chamber 925. Additionally, piston head portion 945 may include a tip portion 994 having a reduced cross-sectional measurement or dimension for more precise volumetric displacement of fluid into and out of pump chamber 925. For example, as shown in FIGS. 5E, 5F, and 5G, the reduced tip portion 994 may include a frustoconical section having a smaller diameter proximal to a tip end 996 of the piston and a larger diameter distal from the tip end 996. If desired, in certain embodiments, an additional seal may optionally be positioned within or proximal to piston barrel 999 (e.g., integrally formed on or attached to a sidewall surface of piston barrel 999) and slidably engaged with a surface of piston head portion 945 thereby reducing the possibility of any substances (e.g., dirt, dried fluid particles, airborne pathogens, etc.) near the cassette 900 from contacting either of slidable seals 946 of the piston head portion 945.

Figure 5G:
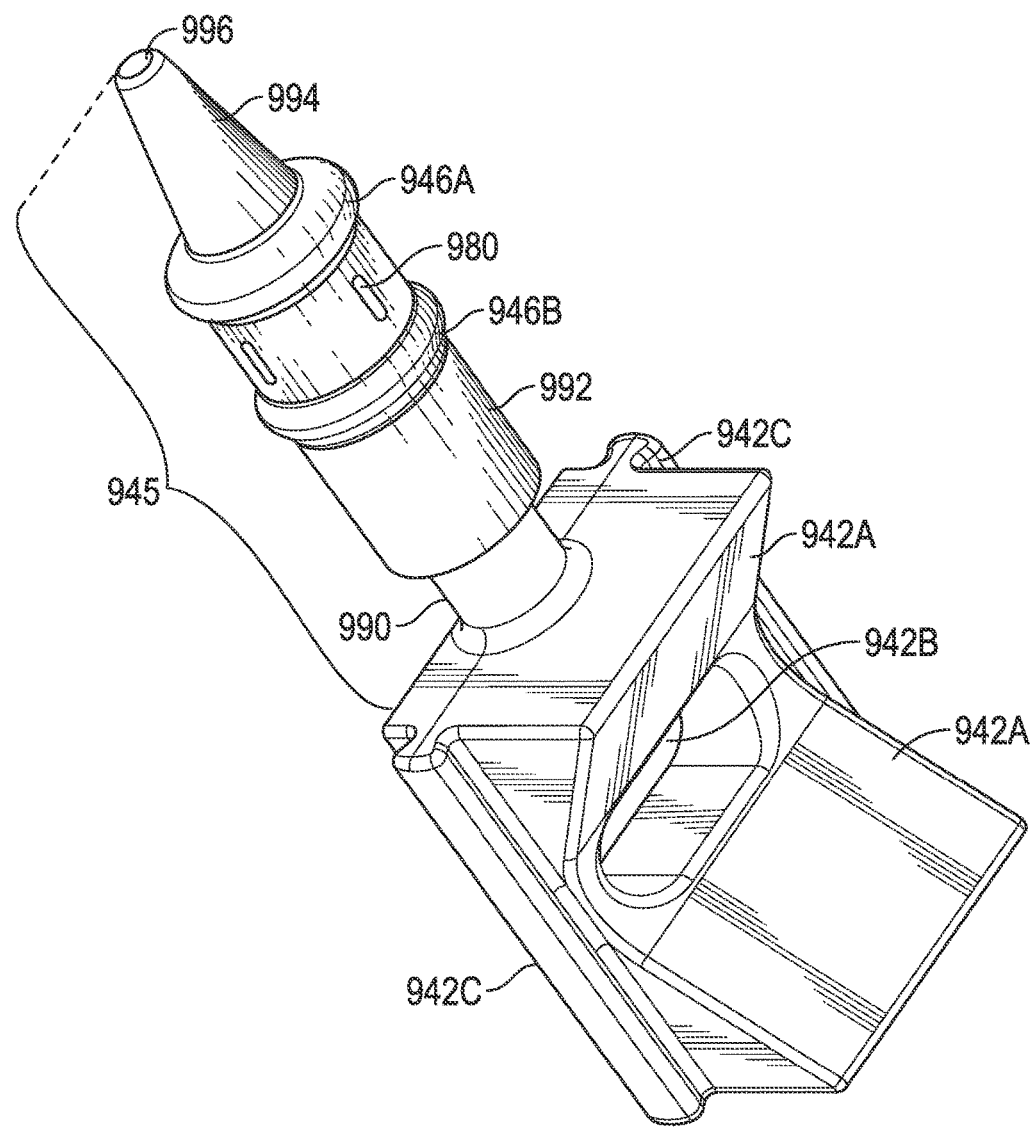
FIG. 5G illustrates a perspective view of an example of another embodiment of a piston of a disposable IV pump cassette, in accordance with aspects of the present disclosure.
Figure 5H:
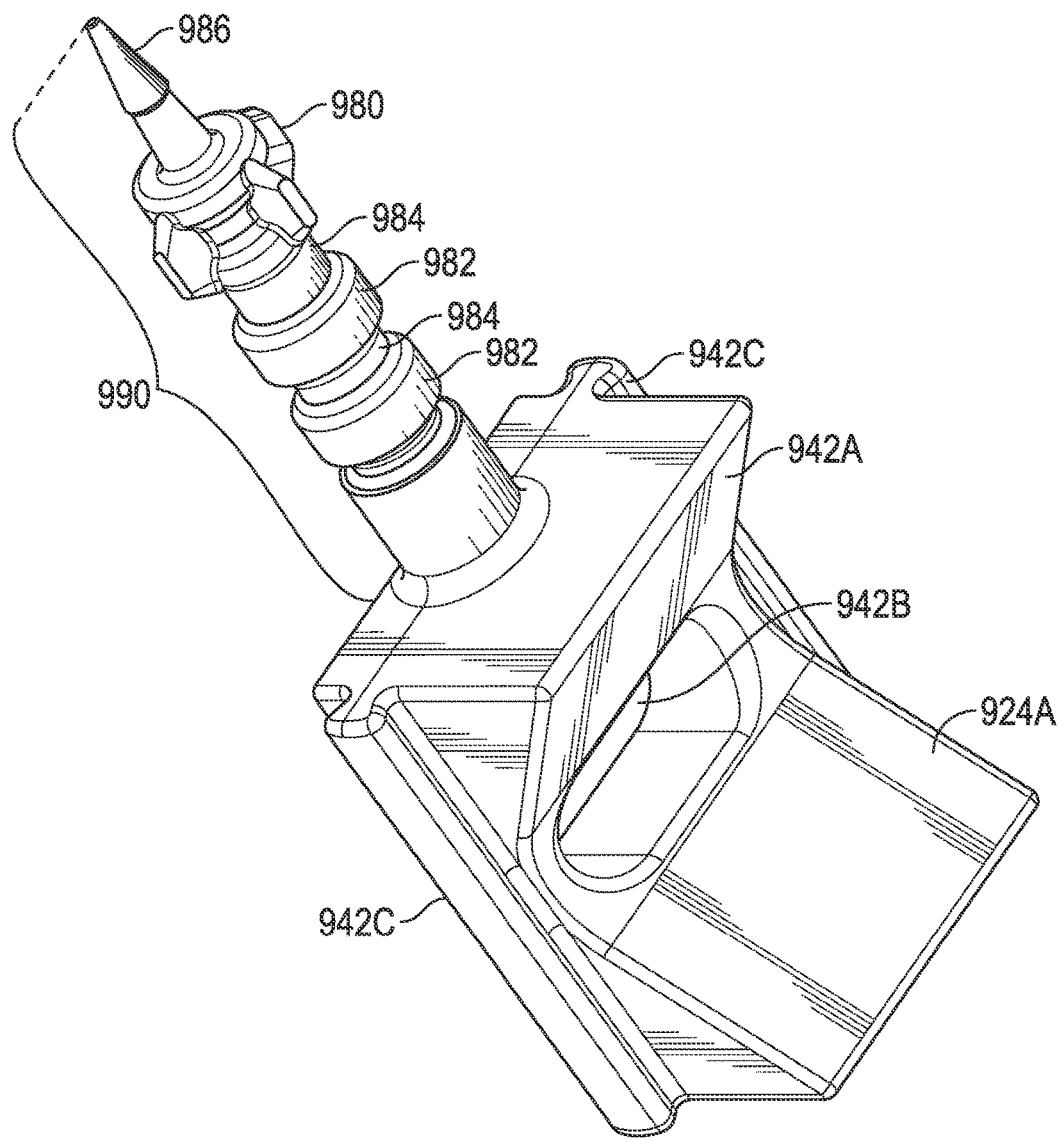
FIG. 5H illustrates a perspective view of the example of the embodiment of the piston FIG. 5G showing a center post of the piston, in accordance with aspects of the present disclosure.
Figure 5I:
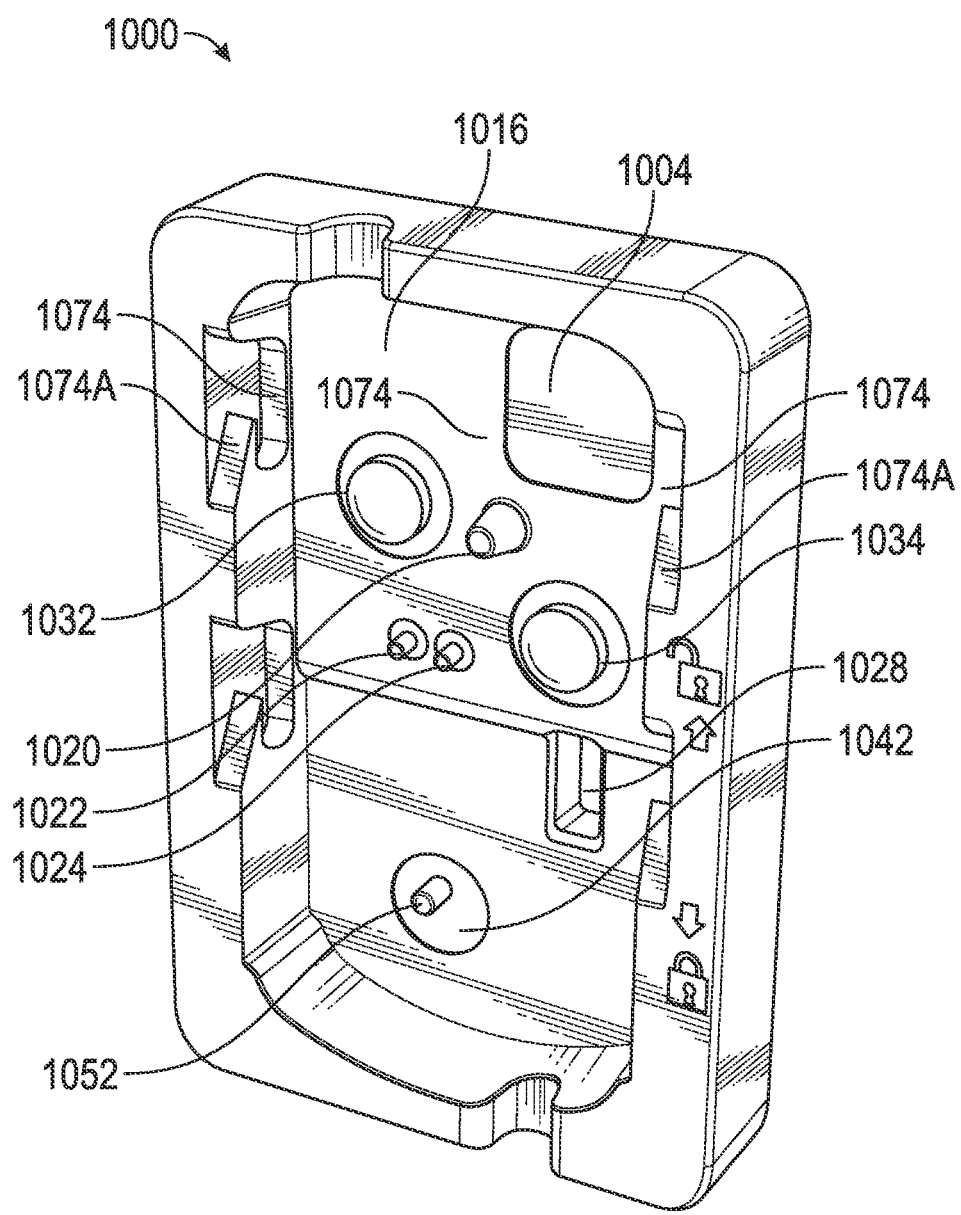
FIG. 5I illustrates a perspective view of the example embodiment of the cassette recess of FIG. 4B, in accordance with aspects of the present disclosure.

As shown in FIG. 5G, in some embodiments, one or more portions of center post 990 such as portions 980 may protrude substantially through sealing member 992 to form a portion of the outer surface of piston head portion 945. In other embodiments, protruding portions of center post 990 may extend only partially into sealing member 992. FIG. 5H shows examples of protrusions 980 extending from center post 990.

As shown in FIG. 5H, center post 990 may extend from and be integrally formed with actuator-receiving portion 942. In the example of FIG. 5H, center post 990 includes protrusions 980 extending perpendicularly from center post 990 (e.g., extending in a direction perpendicular to the direction in which center post extends from actuator-receiving portion 942), a reduced tip portion 986 and a plurality of relatively wider portions 982 interposed along the length of center post 990 with a plurality of relatively narrower portions 984. However, this is merely illustrative and center post may be formed with or without any or all of features 980, 982, 984, and/or 986. For example, in the embodiment shown in FIG. 5E, center post 990 is provided with alternating width portions 982 and 984 and without a tip portion 986.

Tip portion 986 may be configured to extend into and support tip portion 994 of piston head portion 945 and may have a reduced frustoconical shape that corresponds to the reduced frustoconical shape of tip portion 994 of piston head portion 945. Features such as features 980, 982, and 984 on center post 990 may help secure and prevent movement of sealing member 992 (e.g., longitudinal and/or rotational movement) of sealing member 992 relative to center post 990. Features such as perpendicular protrusions 980 may also provide stabilization in the manufacturing process for center post 990 by preventing the post from being pushed off center with respect to actuator-receiving portion (e.g., in an injection molding process).

For example, a pumping operation of infusion pump system 10, 11 when cassette 900 is primed and seated in cassette recess 1000 may comprise activating outlet-side valve actuator 1024 such that outlet-side valve 924 is closed or sealed while activating inlet-side valve actuator 1022 such that inlet-side valve 922 is opened. Opening of inlet-side valve 922 may coincide with or occur shortly after a reverse stroke of piston head portion 945 (e.g., a movement of piston head portion 945 away from pump chamber 925). Accordingly, fluid can flow from upstream pressure dome 932 to pump chamber 925. Alternatively, or in addition to, outlet-side valve 924 may comprise a one-way valve mechanism that permits flow of fluid under normal conditions in one direction (from a fluid container to a patient). Additionally, inlet-side valve 922 may also comprise a one-way valve mechanism permitting flow of fluid in one direction (from a fluid container to a patient) under normal operating conditions. In this configuration, cassette recess 1000 may not need to incorporate either outlet-side valve actuator 1024 or inlet-side valve actuator 1022. Outlet-side valve 924 and inlet-side valve 922 may limit flow of fluid in one direction, but permit flow in an opposite direction in the event fluid pressure overcomes a cracking pressure of the valves.

Continuing with the valve-operated implementation, the pumping operation may comprise activating outlet-side valve actuator 1024 such that outlet-side valve 924 is open while activating inlet-side valve actuator 1022 such that inlet-side valve 922 is closed or sealed. Opening of outlet-side valve 924 may coincide with or occur shortly before a forward stroke of piston head portion 945 (e.g., a movement of piston head portion 945 toward the opening of the pump chamber 925 such that the volume of the pump chamber 925 is reduced). Thus, fluid can flow from pump chamber 925 to downstream pressure dome 934 and consequently urge fluid out outlet 914.

In certain embodiments, pump chamber 925 is a smaller volume than one or both of upstream pressure dome 932 and downstream pressure dome 934. Accordingly, larger and compliant upstream pressure dome 932 and/or downstream pressure dome 934 can address any backpressure issues in the IV set, thereby allowing for an accurate and precise volume of fluid entering pump chamber 925 to be pumped.

Referring to FIGS. 5A-5I, actuator-receiving portion 942 and pump actuator 1042 may be configured as a reciprocating motion mechanism (e.g., a scotch-yoke configuration, a cam-driven (perpendicular motion) configuration, a linear actuator, a rotary actuator, etc.) in certain implementations. Actuator-receiving portion 942 may be accessible by pump actuator 1042 via an aperture through interface-facing sider section 976. In such implementations, actuator-receiving portion 942 may include opposing ramp portions 942a for guiding a circularly rotatable pin 1052 of pump actuator 1042 toward the elongate slot 942b of actuator-receiving portion 942. For example, the outer edges of the opposing ramp portions may be arranged at a distance that will ensure engagement with the circularly rotatable pin 1052 of pump actuator 1042. When the rotatable pin 1052 contacts one of the ramp portions, the actuator-receiving portion 942 will move to align the elongate slot 942b of actuator-receiving portion 942 with the rotatable pin 1052 of pump actuator 1042. As such, the actuator-receiving portion 942 may be sized and positioned to receive the circularly rotatable pin 1052 at all positions of the circularly rotatable pin along a circular path. Additionally, in one embodiment, the elongate slot 942b may have a width similar to the diameter of the circularly rotatable pin. However, this is merely illustrative. In various embodiments, the shape and width of slot 942b may be adjusted to tune the pumping properties of piston 901 in cooperation with pin 1052.

However, it is to be appreciated that other pump drive assemblies are contemplated with cassette 900 and cassette recess 1000 in accordance with the present disclosure.

Although the piston embodiments of FIGS. 5E-5H have been described in the context of the embodiment of pump cassette 900 and corresponding cassette recess 1000 of an interface module, it should be appreciated that the various aspects of the piston embodiments described in connection with FIGS. 5E-5H may be implemented with any suitable configuration of a pump cassette and cassette recess pair (e.g., pump cassette 100 and cassette recess 200 of FIGS. 2A-3C or other pump cassette/cassette recess pairs) or any other fluid control system using a piston pumping operation.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A pump cassette comprising:
a rigid body comprising a frame portion, a base portion, a compliant membrane disposed substantially therebetween, and two opposing longitudinal edge sections, wherein the rigid body comprises a controllable fluid pathway defined in part by the compliant membrane and extending from an inlet port to an outlet port; and
a piston disposed at least partially within the rigid body such that movement of the piston varies a volume of a pump chamber defined within the controllable fluid pathway.

Concept 2. The pump cassette of concept 1 or any other concept, wherein the piston is longitudinally moveable with respect to the rigid body and wherein the piston comprises an actuator-receiving portion.

Concept 3. The pump cassette of concept 2 or any other concept, wherein the actuator-receiving portion comprises opposing ramp portions and an elongate slot.

Concept 4. The pump cassette of concept 3 or any other concept, wherein the opposing ramp portions are disposed such that the opposing ramp portions angle downwardly towards the elongate slot with respect to an interface-facing side of the pump cassette.

Concept 5. The pump cassette of concept 4 or any other concept, wherein the elongate slot is arranged orthogonal to the movement of the piston.

Concept 6. The pump cassette of concept 1 or any other concept, wherein at least one of the base portion or the frame portion includes guiderails for prohibiting rotational movement of the piston within the rigid body.

Concept 7. The pump cassette of concept 1 or any other concept, wherein the piston comprises a reduced tip portion comprising a frustoconical section having a smaller diameter proximal to a tip end of the piston and a larger diameter distal from the tip end.

Concept 8. The pump cassette of concept 1 or any other concept, wherein the piston comprises a first seal proximal to a tip end of the piston, the first seal for providing a sealed movable barrier of the pump chamber.

Concept 9. The pump cassette of concept 8 or any other concept, wherein the piston comprises a second seal distal from the tip end with respect to the first seal, the second seal for providing a sealed movable exterior-facing barrier.

Concept 10. The pump cassette of concept 9 or any other concept, wherein both the first seal and the second seal are circumferential.

Concept 11. The pump cassette of concept 10, wherein the piston comprises:
an actuator-receiving portion;
a center post extending from and integrally formed with the actuator-receiving portion; and
a sealing member disposed on the center post, wherein the first seal and the second seal are integral portions of the sealing member.

Concept 12. The pump cassette of concept 11 or any other concept, wherein the center post extends in a first direction from the actuator-receiving portion and wherein the center post comprises a plurality of protrusions extending in a direction perpendicular to the first direction from the center post at least partially into the sealing member.

Concept 13. A pump cassette comprising:
a rigid body comprising a frame portion, a base portion, a compliant membrane disposed substantially therebetween, and two opposing longitudinal edge sections, wherein the rigid body comprises a controllable fluid pathway defined in part by the compliant membrane and extending from an inlet port to an outlet port;
a piston disposed at least partially within the rigid body, the piston comprising an actuator-receiving portion; and
a slider coupled to the two opposing longitudinal edge sections and longitudinally articulable with respect to the rigid body.

Concept 14. The pump cassette of concept 13 or any other concept, wherein the slider comprises an interface-facing portion that extends around an area of the rigid body adjacent to the actuator-receiving portion of the piston and provides an opening for access to the actuator-receiving portion.

Concept 15. The pump cassette of concept 13 or any other concept, wherein the actuator-receiving portion of the piston is a pump drive mechanism operably accessible from an exterior of the pump cassette such that movement of the actuator-receiving portion causes the piston to vary a volume of a pump chamber defined within the controllable fluid pathway.

Concept 16. An infusion pump system comprising:
a processing unit;
a cassette recess comprising:
a circularly moveable actuator mechanism disposed proximate to a back surface of the cassette recess and operably coupled to the processing unit, and
a plurality of cassette engagement slots,
wherein the cassette recess is adapted to receive a pump cassette comprising:
a rigid body comprising a compliant membrane, wherein the rigid body comprises a controllable fluid pathway extending from an inlet port to an outlet port, and
a piston disposed at least partially within the rigid body such that movement of the piston varies a volume of a pump chamber defined within the controllable fluid pathway.

Concept 17. The infusion pump system 16 or any other concept, wherein the piston comprises an actuator-receiving portion such that when the pump cassette engages with the cassette recess, the actuator-receiving portion is sized and positioned to receive an actuator rod of the circularly moveable actuator mechanism for all positions of the actuator rod along a circular path.

Concept 18. The infusion pump system of concept 17 or any other concept, wherein the actuator-receiving portion comprises opposing ramp portions and an elongate slot having a width similar to a diameter of the actuator rod.

Concept 19. The infusion pump system of concept 17 or any other concept, wherein the actuator-receiving portion comprises guiderails for engaging with guideslots disposed on the rigid body.

Concept 20. The infusion pump system of concept 17 or any other concept, wherein the piston comprises a first seal proximal to a tip end of the piston, the first seal for providing a sealed movable barrier of the pump chamber, and a second seal distal from the tip end with respect to the first seal, the second seal for providing a sealed movable exterior-facing barrier.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A pump cassette comprising:
   a rigid body comprising a frame portion, a base portion, a compliant membrane disposed substantially therebetween, and two opposing longitudinal edge sections, wherein the rigid body comprises a controllable fluid pathway defined in part by the compliant membrane and extending from an inlet port to an outlet port; and
   a piston disposed at least partially within the rigid body such that movement of the piston varies a volume of a pump chamber defined within the controllable fluid pathway,
   wherein the piston comprises a first seal that provides a sealed movable barrier of the pump chamber and a second seal that provides a sealed movable exterior-facing barrier,
   wherein the first seal is disposed at a distance from the second seal that is longer than a stroke of the piston such that a first path of the first seal does not overlap a second path of the second seal.

2. The pump cassette of claim 1, wherein at least one of the base portion or the frame portion includes guiderails for prohibiting rotational movement of the piston within the rigid body.

3. The pump cassette of claim 1, further comprising a piston barrel in the rigid body, at least a portion of the piston barrel adjacent to and fluidly coupled with a portion of the fluid pathway, wherein the first seal is disposed in slidable contact with an internal wall of the piston barrel.

4. The pump cassette of claim 1, wherein the piston comprises a reduced tip portion comprising a frustoconical section having a smaller diameter proximal to a tip end of the piston and a larger diameter distal from the tip end.

5. The pump cassette of claim 1, wherein the piston is longitudinally moveable with respect to the rigid body and wherein the piston comprises an actuator-receiving portion.

6. The pump cassette of claim 5, wherein the actuator-receiving portion comprises opposing ramp portions and an elongate slot.

7. The pump cassette of claim 6, wherein the opposing ramp portions are disposed such that the opposing ramp portions angle downwardly towards the elongate slot with respect to an interface-facing side of the pump cassette.

8. The pump cassette of claim 7, wherein the elongate slot is arranged orthogonal to the movement of the piston.

9. The pump cassette of claim 1, wherein the first seal is disposed proximal to a tip end of the piston.

10. The pump cassette of claim 9, wherein the second seal is distal from the tip end with respect to the first seal.

11. The pump cassette of claim 10, wherein both the first seal and the second seal are circumferential.

12. The pump cassette of claim 11, wherein the piston comprises:
  an actuator-receiving portion;
  a center post extending from and integrally formed with the actuator-receiving portion; and
  a sealing member disposed on the center post, wherein the first seal and the second seal are integral portions of the sealing member.

13. The pump cassette of claim 12, wherein the center post extends in a first direction from the actuator-receiving portion and wherein the center post comprises a plurality of protrusions extending in a direction perpendicular to the first direction from the center post at least partially into the sealing member.

14. An infusion pump system comprising:
a processing unit;
a cassette recess comprising:
  a circularly moveable actuator mechanism disposed proximate to a back surface of the cassette recess and operably coupled to the processing unit, and
  a plurality of cassette engagement slots,
wherein the cassette recess is adapted to receive a pump cassette comprising:
a rigid body comprising a frame portion, a base portion, a compliant membrane disposed substantially therebetween, and two opposing longitudinal edge sections, wherein the rigid body comprises a controllable fluid pathway defined in part by the compliant membrane and extending from an inlet port to an outlet port, and
a piston disposed at least partially within the rigid body such that movement of the piston varies a volume of a pump chamber defined within the controllable fluid pathway, wherein the piston comprises a first seal that provides a sealed movable barrier of the pump chamber and a second seal that provides a sealed movable exterior-facing barrier, wherein the first seal is disposed at a distance from the second seal that is longer than a stroke of the piston such that a first path of the first seal does not overlap a second path of the second seal.

15. The infusion pump system of claim 14, wherein the piston comprises an actuator-receiving portion such that when the pump cassette engages with the cassette recess, the actuator-receiving portion is sized and positioned to receive an actuator rod of the circularly moveable actuator mechanism for all positions of the actuator rod along a circular path.

16. The infusion pump system of claim 15, wherein the actuator-receiving portion comprises opposing ramp portions and an elongate slot having a width similar to a diameter of the actuator rod.

17. The infusion pump system of claim 15, wherein the actuator-receiving portion comprises guiderails for engaging with guideslots disposed on the rigid body.

18. The infusion pump system of claim 15, wherein first seal is proximal to a tip end of the piston, and wherein the second seal is distal from the tip end with respect to the first seal.

* * * * *